United States Patent
Shih et al.

(10) Patent No.: US 10,752,657 B2
(45) Date of Patent: *Aug. 25, 2020

(54) ANTIMICROBIAL PEPTIDES DERIVED FROM HEPATITIS B VIRUS CORE PROTEIN ARGININE-RICH DOMAIN

(71) Applicant: Academia Sinica, Taipei (TW)

(72) Inventors: Chiaho Shih, Taipei (TW); Heng-Li Chen, Taipei (TW); Pei-Yi Su, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/258,115

(22) Filed: Jan. 25, 2019

(65) Prior Publication Data
US 2019/0153042 A1 May 23, 2019

Related U.S. Application Data

(62) Division of application No. 14/766,359, filed as application No. PCT/US2014/014938 on Feb. 5, 2014, now Pat. No. 10,214,564.

(60) Provisional application No. 61/761,650, filed on Feb. 6, 2013.

(51) Int. Cl.
| | | |
|---|---|---|
| *C07K 14/005* | (2006.01) | |
| *A61K 39/12* | (2006.01) | |
| *A61K 39/29* | (2006.01) | |
| *C12N 7/00* | (2006.01) | |
| *A61K 38/00* | (2006.01) | |

(52) U.S. Cl.
CPC ............ *C07K 14/005* (2013.01); *A61K 39/12* (2013.01); *A61K 39/292* (2013.01); *C12N 7/00* (2013.01); *A61K 38/00* (2013.01); *C12N 2730/10133* (2013.01); *C12N 2730/10134* (2013.01)

(58) Field of Classification Search
None
See application file for complete search history.

(56) References Cited

U.S. PATENT DOCUMENTS

| 6,060,595 A | 5/2000 | Scaglioni et al. |
| 7,244,706 B2 | 7/2007 | Mann |

FOREIGN PATENT DOCUMENTS

| WO | WO-2004/050883 A2 | 6/2004 |
| WO | WO-2014/124047 A1 | 8/2014 |

OTHER PUBLICATIONS

UniprotKB-A0A165YEV4 (Jul. 6, 2016).*
Merck Manual (https://www.mercknnanuals.com/professional/infectious-diseases/viruses/overview-of-viruses accessed Feb. 19, 2019).*
Merck Manual (https://www.mercknnanuals.com/home/skin-disorders/fungal-skin-infections/overview-of-fungal-skin-infections accessed Feb. 19, 2019).*
Brandenburg et al "Antimicrobial Peptides: Multifunctional Drugs for Different Applications" Polymers vol. 4, pp. 539-560, 2012.
Chen et al "Identification of a Novel Antimicrobial Peptide from Human Hepatitis B Virus Core Protein Arginine-Rich Domain (ARD)" Pathogens vol. 9, pp. 1-16.
Chen et al "Improvement of In Vivo Antimicrobial Activity of HBcARD Peptides by D-Arginine Replacement" Applied Microbiology and Biotechnology vol. 100, pp. 9125-9132, 2016.
Chu et al "Nucleic Acid Chaperone Activity Associated with the Arginine-Rich Domain of Human Hepatitis B Virus Core Protein" Journal of Virology vol. 88, pp. 2530-2543, 2014.
Fee et al "Protein PEGylation: An Overview of Chemistry and Process Considerations" EPR vol. 1, 2010.
Isdro-Llobet et al "Amino-Acid Protecting Groups" Chemistry Review vol. 109, pp. 2455-2504, 2009.
Jung et al "C-Terminal Substitution of HBV Core Proteins with Those from DHBV Reveals that Arginine-Rich $^{167}$RRRSQSPRR$^{175}$ Domain is Critical for HBV Replication" One vol. 7, pp. 1-14, 2012.
Li et al "Nuclear Export and Import of Human Hepatitis B Virus Capsid Protein and Particles" PLOS Pathogens vol. 6, pp. 1-17, 2010.
Miura et al "Basic Peptide Protamine Exerts Antimicrobial Activity Against Periodontopathic Bacteria" Journal of Biomedical Science and Engineering vol. 3, pp. 1069-1072, 2010.
Protective Groups for Peptide Synthesis [online], Peptide Guide 2012 [retrieved on May 25, 2014]. Retrieved from the internet: http://peptideguide.com/protecting-groups-spps.html, p. 1; p. 1, paragraphs 2-3.
Akbar et al "Strong and Multi-Antigen Specific Immunity by Hepatitis B Core Antigen (HBcAg)-Based Vaccines in a Murine Model of Chronic Hepatitis B: HBcAg is a Candidate for Therapeutic Vaccine Against Hepatitis B Virus" Antiviral Research vol. 96, pp. 59-64, 2012.
Albada et al "Modulating the Activity of Short Arginine-Tryptophan Containing Antibacterial Peptides with N-Terminal Metallocenoyl Groups" Beilstein Journal of Organic Chemistry vol. 8, pp. 1753-1764, 2012.
Hamamoto et al "Antimicrobial Activity and Stability to Proteolysis of Small Linear Cationic Peptides with D-Amino Acid Substitutions" Microbiology and Immunology vol. 46, pp. 741-749, 2002.
Veiga et al "Arginine-Rich Self-Assembling Peptides as Potent Antibacterial Gels" Biomaterials vol. 33, pp. 8907-8916, 2012.

* cited by examiner

*Primary Examiner* — James H Alstrum-Acevedo
*Assistant Examiner* — Tara L Martinez
(74) *Attorney, Agent, or Firm* — Cesari and McKenna, LLP

(57) ABSTRACT

A pharmaceutical composition comprising: (a) an isolated peptide, wherein the peptide includes three or four arginine-rich domains (ARDs) from the carboxy-terminal region of hepatitis B virus core protein (HBc) and exhibits an antimicrobial activity; and (b) a pharmaceutically acceptable carrier.

12 Claims, 8 Drawing Sheets

Specification includes a Sequence Listing.

FIG. 1
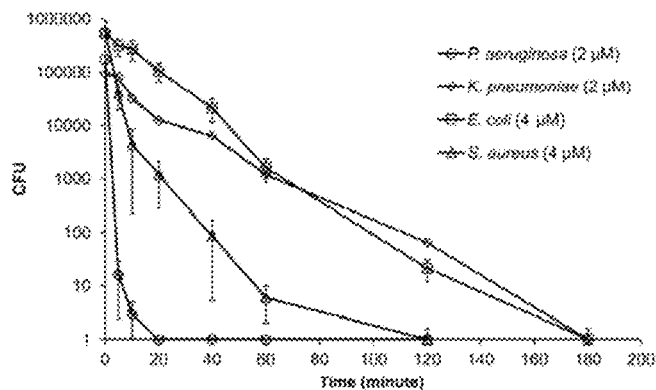
FIG. 2
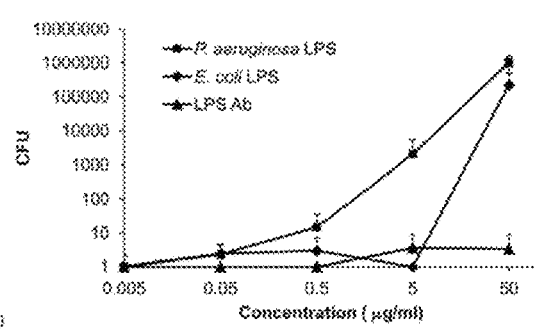
FIG. 5

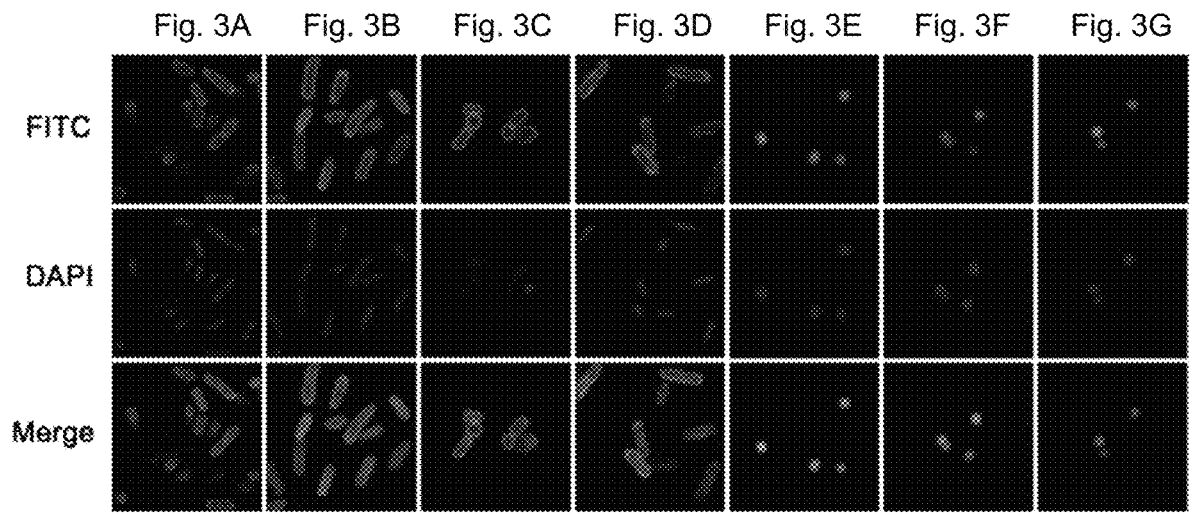
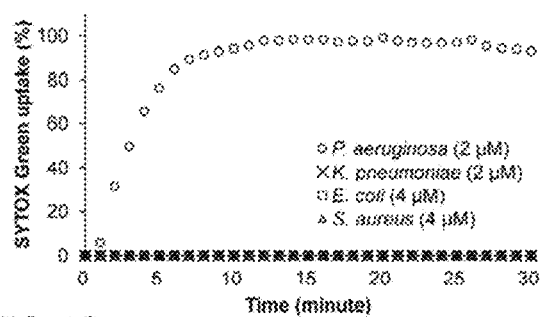
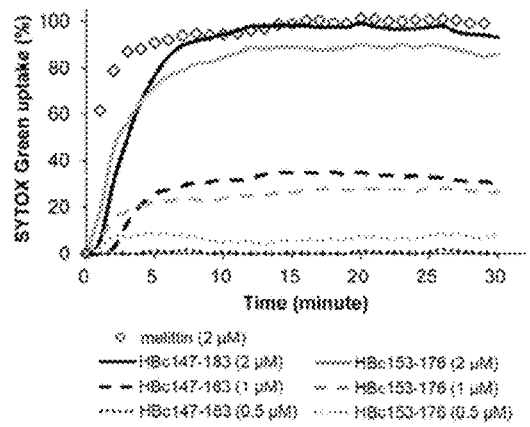
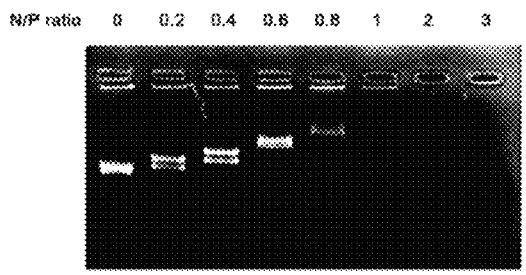

Fig. 6A
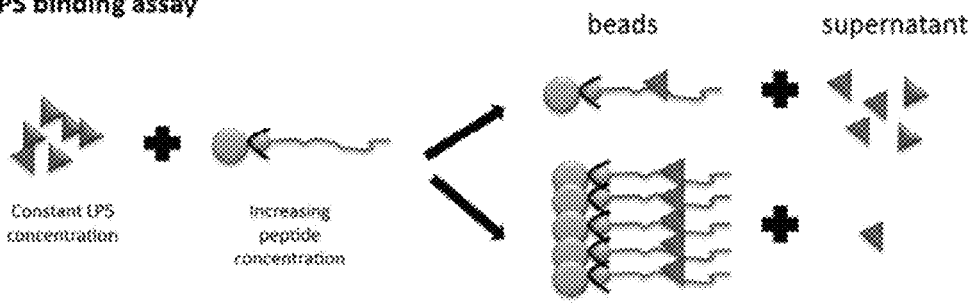
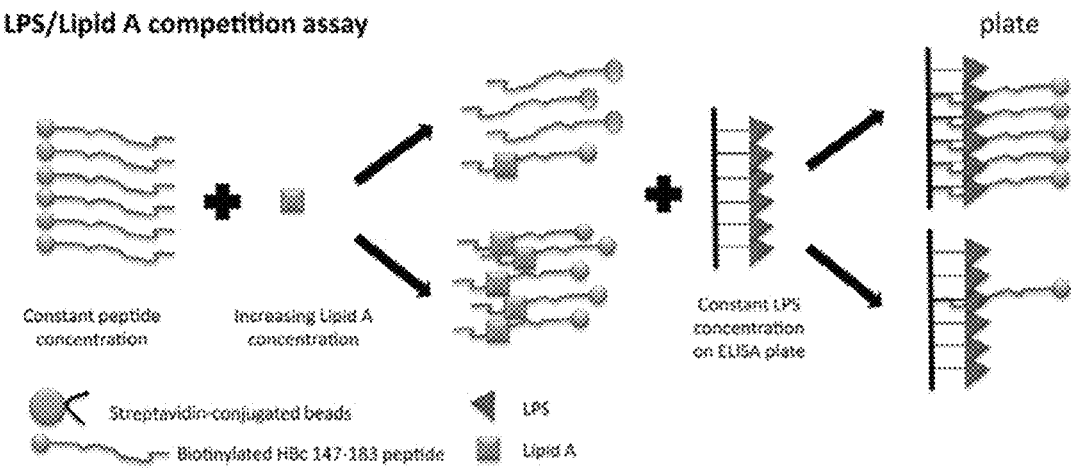
Fig. 6B
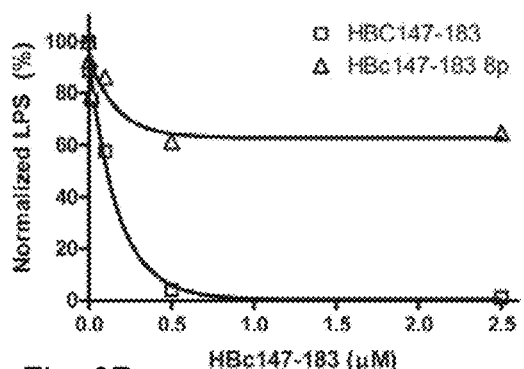
Fig. 6C
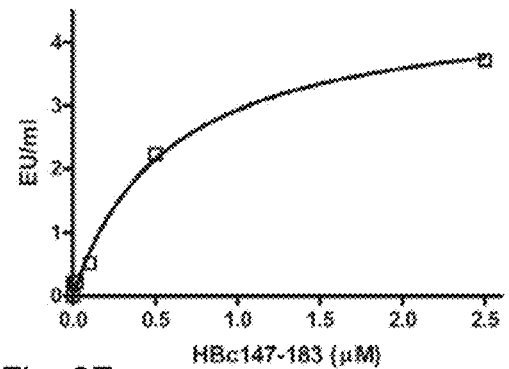
Fig. 6D
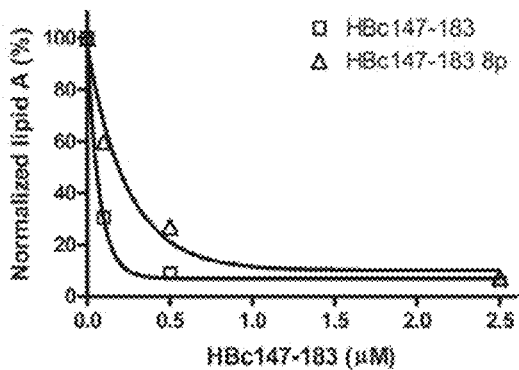
Fig. 6E
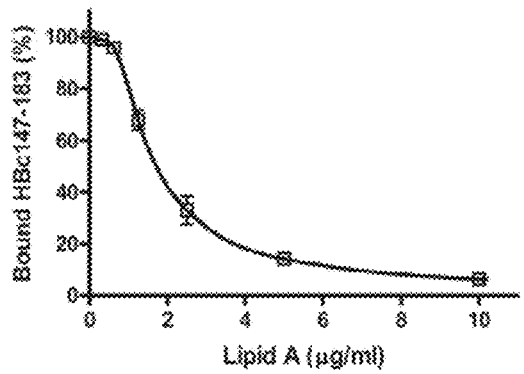

Fig. 7A
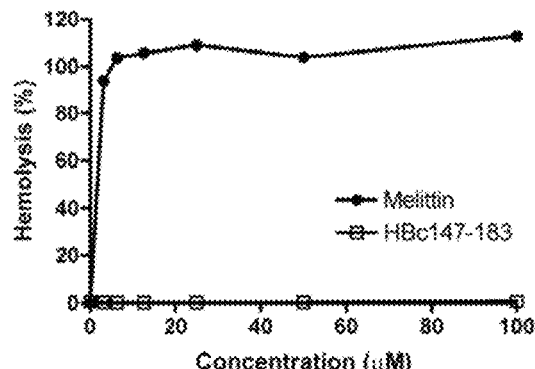
Fig. 7B
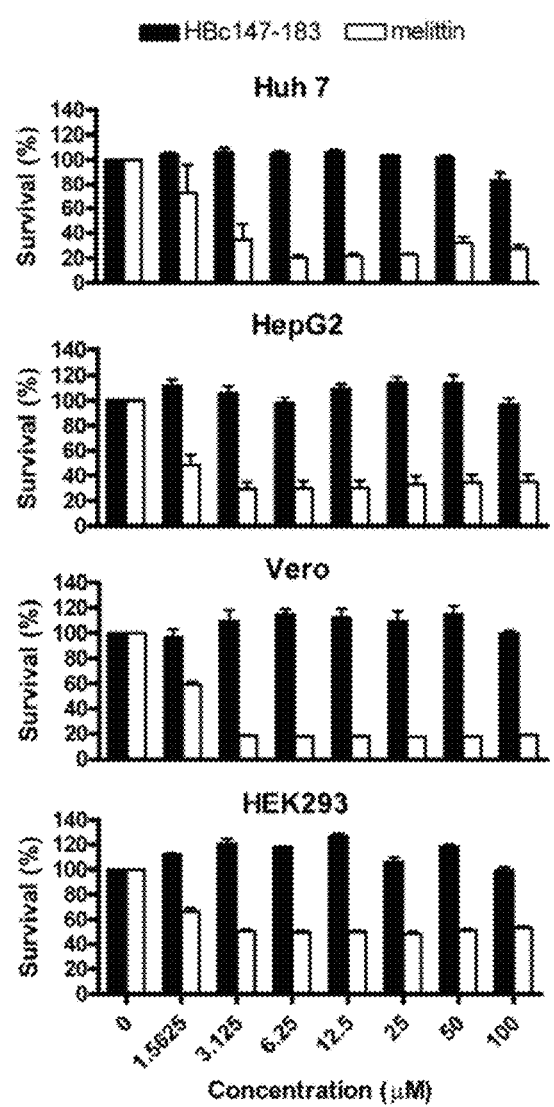
Fig. 7.C
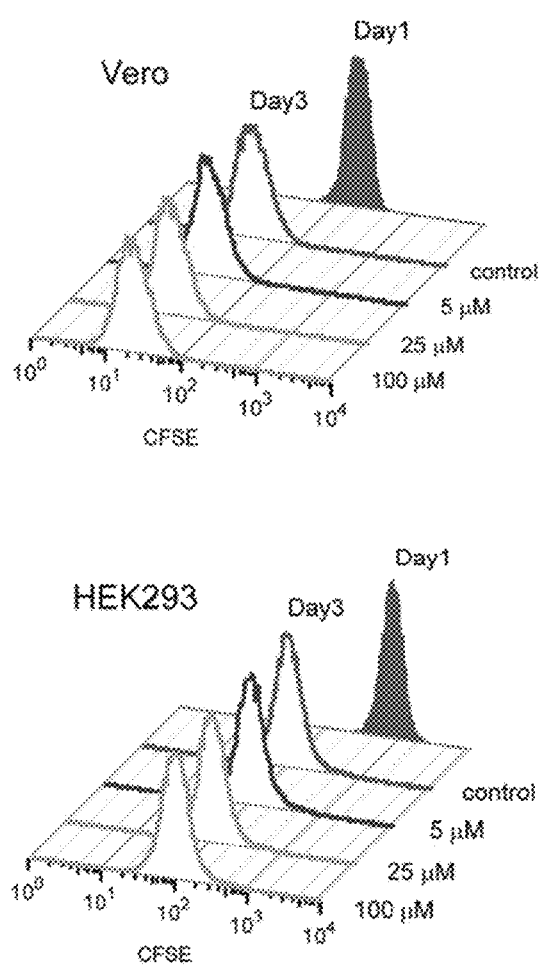
Fig. 7D
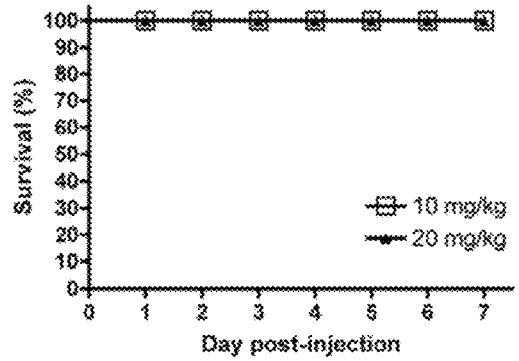

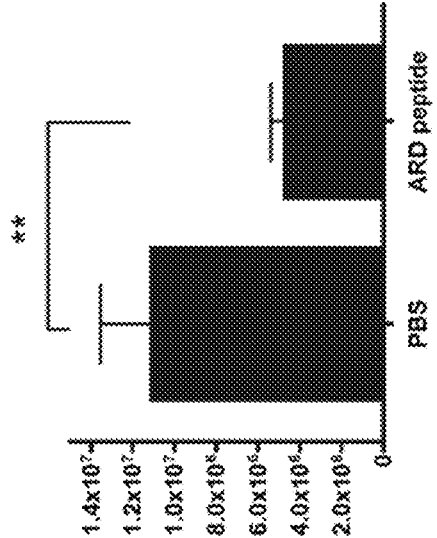

FIG. 9A

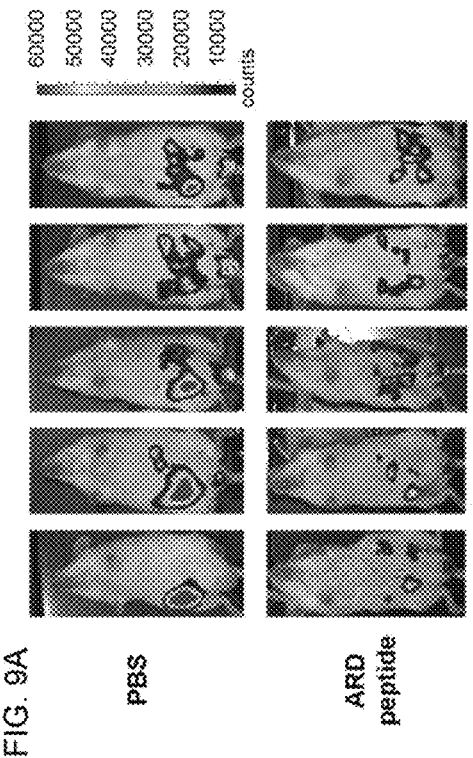

FIG. 9B

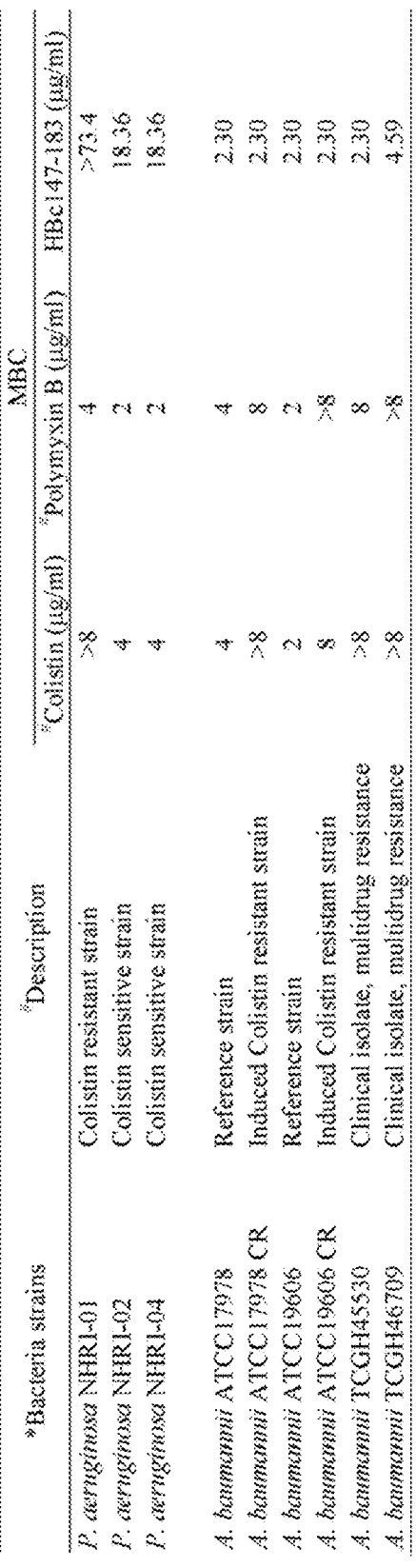

FIG. 11

Antimicrobial activity of ARD peptide HBc147-183 against colistin-resistant and sensitive *P. aeruginosa* and *A. baumannii*.

| *Bacteria strains | #Description | MBC | | |
|---|---|---|---|---|
| | | #Colistin (μg/ml) | #Polymyxin B (μg/ml) | HBc147-183 (μg/ml) |
| *P. aeruginosa* NHRI-01 | Colistin resistant strain | >8 | 4 | >73.4 |
| *P. aeruginosa* NHRI-02 | Colistin sensitive strain | 4 | 2 | 18.36 |
| *P. aeruginosa* NHRI-04 | Colistin sensitive strain | 4 | 2 | 18.36 |
| *A. baumannii* ATCC17978 | Reference strain | 4 | 4 | 2.30 |
| *A. baumannii* ATCC17978 CR | Induced Colistin resistant strain | >8 | 8 | 2.30 |
| *A. baumannii* ATCC19606 | Reference strain | 2 | 2 | 2.30 |
| *A. baumannii* ATCC19606 CR | Induced Colistin resistant strain | 8 | >8 | 2.30 |
| *A. baumannii* TCGH45530 | Clinical isolate, multidrug resistance | >8 | 8 | 2.30 |
| *A. baumannii* TCGH46709 | Clinical isolate, multidrug resistance | >8 | >8 | 4.59 |

*Colistin-sensitive and -resistant *P. aeruginosa* were obtained from NHRI, Taiwan, and colistin-sensitive and -resistant *A. baumannii* were obtained Tzu-Chi Buddhist General Hospital, Taiwan (31; Materials and Methods).

The breakpoints of colistin and polymyxin B resistance are according to Clinical and Laboratory Standards Institute (CLSI) (2009).

FIG. 10

Antimicrobial activity of HBC ARD peptides

| Peptide | Antimicrobial activity<sup>a</sup> μM (μg/ml) | | | | | | | |
|---|---|---|---|---|---|---|---|---|
| | Gram-negative bacteria | | | | Gram-positive bacteria | | | Fungi |
| | P. aeruginosa (ATCC 9027)<sup>b</sup> | P. aeruginosa (ATCC 27853) | K. pneumoniae (ATCC 13884) | E. coli (ATCC 25922) | S. aureus (ATCC 19636)<sup>c</sup> | S. aureus (ATCC 25923)<sup>c</sup> | S. aureus (ATCC 29213)<sup>c</sup> | C. albicans (ATCC 10231) |
| HBc147-183 | 2 (9.18) | 2-4 (9.18-18.36) | 2 (9.18) | 4 (18.36) | 4 (18.36) | 4 (18.36) | 4 (18.36) | ~8 (~36.7) |
| HBc147-175 | 0.5 (1.84) | 1 (3.68) | 1 (3.68) | 1 (3.68) | >32 (>117.86) | >32 (>117.86) | >32 (>117.86) | ~8 (~36.7) |
| HBc147-167 | >32 (>85) | >32 (>85) | 8 (21.3) | >32 (>85) | ND | ND | ND | ND |
| HBc147-159 | ND | ND | ND | ND | ND | ND | ND | ND |
| HBc153-176 | 1-2 (3-6) | 1-2 (3-6) | >32 (>96) | 16 (48) | ND | ND | ND | ND |
| HBc157-176 | 2 (5.2) | 2 (5.2) | >32 (>83.36) | >32 (>86.46) | ND | ND | ND | ND |
| HBc164-176 | ND | ND | ND | ND | ND | ND | ND | ND |
| HBc153-175 | 2 (6.8) | 2 (6.8) | >32 (>93.28) | 16 (46.64) | ND | ND | ND | ND |
| HBc157-175 | 2 (5.4) | 16 (43.23) | >32 (>86.46) | >32 (>86.46) | ND | ND | ND | ND |
| HBc162-175 | 2 (10) | >32 (>80.59) | >32 (>80.59) | >32 (>80.59) | ND | ND | ND | ND |
| HBc155p | 8 (37.4) | 8 (37.4) | 1 (4.97) | 8 (37.4) | 8 (37.4) | 8 (37.4) | 8 (37.4) | ND |
| HBc162p | ~32 (~149.5) | ~32 (~149.5) | ~32 (~149.5) | ~32 (~149.5) | ~32 (~149.5) | ~32 (~149.5) | ~32 (~149.5) | ND |
| HBc170p | ~32 (~149.5) | ~32 (~149.5) | 8 (37.4) | ~32 (~149.5) | ~32 (~149.5) | ~32 (~149.5) | ~32 (~149.5) | ND |
| HBc176p | 8 (37.4) | 8 (37.4) | 4 (18.68) | 8 (37.4) | 8 (37.4) | 8 (37.4) | 8 (37.4) | ND |
| HBc181p | 2 (9.3) | 4 (18.68) | 4 (18.68) | 4 (18.68) | 4 (18.68) | 4 (18.68) | 4 (18.68) | ND |
| HBc155p162p170p | >32 (>154.5) | >32 (>154.5) | >32 (>154.5) | >32 (>154.5) | >32 (>154.5) | >32 (>154.5) | >32 (>154.5) | ND |
| HBc147-183(34AA) | 32 (135.94) | 32 (135.94) | 32 (135.94) | >32 (>135.94) | >32 (>135.94) | >32 (>135.94) | >32 (>135.94) | ND |
| Melittin | 2 (5.7) | 2 (5.7) | 2 (5.7) | 2 (5.7) | 1 (2.85) | 1 (2.85) | 1 (2.85) | 4 (11.4) |

<sup>a</sup>Antimicrobial activity were measured after incubation with peptides for 3 hours. Numbers here represent MBC (minimal bactericidal concentration). ND, not detectable.
<sup>b</sup>Ampicillin-resistant Pseudomonas aeruginosa Magulla strain
<sup>c</sup>Methicillin-resistant Staphylococcus aureus subsp. strain

FIG. 12

```
                          (SEQ ID NO: )      10         20         30
                                       ....|....| ....|....| ....|....| ....|....
HBV adr/Japan/Nishio       18          TVVRRR--GR SPRRRTPSPR RRRSKSPRRR RSQSRESQC
HBV adr/Japan/A4/199       19          TVVRRR--GR SPRRRTPSPR RRRSQSPRRR RSQSRESQC
                                                            SEQ ID NO: 13  SEQ ID NO: 13
HBV adw/Philippino/P       20          TVVRRRDGR  SPRRRTPSPR RRRSQSPRRR RSQSRESQC
HBV adw/Japan/PJDW23       21          TVVRRR--GR SPRRRTPSPR RRRSQSPRRR RSQSRESQC
HBV adw/Okinawa/PODW       22          TVVRRR--GR SPRRRTPSPR RRRSQSPRRR RSQSRESQC
HBV adw/991                23          TVVRRRDGR  SPRRRTPSPR RRRSQSPRRR RSQSRESQC
HBV adw/Indonesia/PI       24          TVVRRR--GR SPRRRTPSPR RRRSQSPRRR RSQSRESQC
HBV adw/China/patien       25          AVVRRR--GR SPRRRTPSPR RRRSQSPRRR RSQSRGSQC
HBV adw/Japan/Nishio       26          TVVRRRDGR  SPRRRTPSPR RRRSQSPRRR RSQSRESQC
                                                            SEQ ID NO: 15
HBV ayw/France/Tioll       27          TVVRRR--GR SPRRRTPSPR RRRSQSPRRR RSQSRESQC
HBV ayw/Australia/Au       28          TVVRQR--GR TIRRRTPSPR RRRSQSPRRR RSQSRESQC
HBV ayw/Japan/JYW796       29          TVVRRR--GR SPRRRTPSPR RRRSQSPRRR RSQSRESQC
HBV ayw/Italy/CI/199       30          TVVRRR--GR SPRRRTPSPR RRRSQSPRRR RSQSRESQC
HBV ayw/China/Tibet1       31          TVVRRR--GR SPRRRTPSPR RRRSQSPRRR RSQSRESQC
HBV ayw/Australia/Au       32          TVVRRR--GR SPRRRTPSPR RRRSQSPRRR RSQSRESQC
HBV ayw/Japan/Ehime        33          TVVRGR--GR SSRRRTPSPR RRRSQSPRRR RSQSRESQC
                                                            SEQ ID NO: 14   SEQ ID NO: 16
```

FIG. 13A

```
                        I         II        III        IV
                        10         20         30         40
                 ....|....| ....|....| ....|....| ....|....| ...
Human            TVVRRRG-   ----RSPRRR TPSPRRRRSQSP RRRRSQS-RE SQC (SEQ ID NO: 1)
Woolly monkey    TVVRRR--   ----RPSGRR TPSPRRRRSQSP RRRRSQS-PA SSC (SEQ ID NO: 2)
Ground squirrel  TVIRRRGS   ARVVKSPRRR TPSPRRRRSQSP RRR-PQS-PA SNC (SEQ ID NO: 3)
Woodchuck        TVIRRRGG   ARASRSPRRR TPSPRRRRSQSP RRRRSQS-PS ANC (SEQ ID NO: 4)
Bat              TIVRRRGG   SPATRSPRRR TPSPRRRRSQSP RRRRSQSPAS SNC (SEQ ID NO: 5)
```

FIG. 13B

```
                 I        II            III         IV
Duck             RKPRGL   EPRRRKVKTT    VVYGRRRSKS  RERRAPTPQR  (SEQ ID NO: 6)
Heron            RKPRGL   EPRRRKVKTT    VVYGRRRSKS  RGRRSPSQR   (SEQ ID NO: 7)
Parrot           RKPRGL   EPRRRKVKTT    VVYGRRRSKS  RERSSSPQR   (SEQ ID NO: 8)
Ross's goose     RKPRGL   EPRRRKVKTT    VVYGRRRSKS  RERRAPTPQR  (SEQ ID NO: 9)
Snow goose       RKPRGL   EPRRRKVKTT    VVYGRRRSKS  RERRASSPQR  (SEQ ID NO: 10)
```

ANTIMICROBIAL PEPTIDES DERIVED FROM HEPATITIS B VIRUS CORE PROTEIN ARGININE-RICH DOMAIN

CROSS REFERENCE TO RELATED APPLICATIONS

This is a divisional application of U.S. application Ser. No. 14/766,359, filed on Aug. 6, 2015, which is the US national stage of International Patent Application No. PCT/US2014/014938, filed on Feb. 5, 2014, which claims priority to U.S. Provisional Application No. 61/761,650, filed on Feb. 6, 2013. The contents of all prior applications are hereby incorporated by reference herein in their entirety.

FIELD OF THE INVENTION

The present invention relates to antimicrobial peptides.

BACKGROUND OF THE INVENTION

The increase of drug-resistant pathogens caused by the extensive use of traditional antibiotics is a serious concern worldwide. There is an urgent need to develop more effective treatment to overcome the drug-resistance problem. Antimicrobial peptides (AMP) are a new class of antibiotics with a new mode of action and remarkable therapeutic effects. In general, they contain 10-50 amino acids, with an overall positive charge and an amphipathic structure. It is well known that most AMPs can directly bind to bacteria membrane and kill them by disrupting membrane or targeting intracellular components. Most importantly, they are effective to antibiotics-resistant pathogens. This unique feature has encouraged the development of AMPs as novel antibiotics in the last few decades.

Prior to the present invention, no literature has reported that peptides derived from hepatitis B virus core protein (HBc) possess antimicrobial activities. Hepatitis B virus core protein (21 KDa) is essential for viral replication. It contains a capsid assembly domain at N-terminus (residue 1 to 149) and an arginine-rich domain (ARD) at C-terminus (residues 150 to 183) (Birnbaum et al. (1990) J Virol 64: 3319-3330; Nassal M (1992) J Virol 66: 4107-4116). ARD contains 16 arginines separated into four arginine-rich clusters (ARD I, II, III, IV) and has a function of binding to nucleic acids. When it binds to HBV pre-genomic RNA or polyanions, HBc can assemble into a stable capsid. In addition, ARD contains important signals for nuclear export and import of HBc core protein and particles. It was unexpectedly discovered that the growth of E. coli expressing HBc1-183 was much slower than that of E. coli expressing HBc1-149 (unpublished results).

SUMMARY OF THE INVENTION

In one aspect, the invention relates to a pharmaceutical composition comprising:
(a) an effective amount of an isolated peptide, wherein the peptide comprises the arginine-rich carboxy-terminal region of hepatitis B virus core protein (HBc) and exhibits an antimicrobial activity; and
(b) a pharmaceutically acceptable carrier.

In another aspect, the invention relates to a pharmaceutical composition comprising:
(a) an effective amount of an isolated peptide comprising a fragment of HBc, the fragment comprising more than one arginine-rich domain (ARD) selected from the group consisting of (i), (ii) and (iii) as follows:
(i) HBc ARD I-IV;
(ii) HBc ARD I-III; or
(iii) HBc ARD II-IV;
wherein the peptide exhibits an antimicrobial activity; and
(b) a pharmaceutically acceptable carrier.

In another aspect, the invention relates to a pharmaceutical composition comprising an effective amount of an isolated peptide, the peptide comprising an arginine-rich sequence derived from the C-terminal region of hepatitis B virus core protein (HBc), wherein the peptide is characterized by having an antimicrobial activity.

Further in another aspect, the invention relates to a pharmaceutical composition as aforementioned for use in killing and/or inhibiting the growth and/or proliferation of a microorganism by causing the composition as aforementioned to be in contact with the microorganism.

Yet in another aspect, the invention relates to a pharmaceutical composition as aforementioned for use in killing and/or inhibiting the growth and/or proliferation of a microorganism in a subject in need thereof, or for treating a subject afflicted with a microbial infection. The subject is afflicted with Staphylococcus aureus or K. pneumoniae infection.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1 shows amino acid sequences of various HBc ARD peptides tested for bactericidal activity. The lower panel presents various phosphorylated peptides and an R-to-A mutant peptide with a total of four Arg-to-Ala substitutions in ARD-III and ARD-IV of HBc147-183.

FIG. 2 shows killing kinetics of HBc147-183 against P. aeruginosa, K. pneumoniae, E. coli and S. aureus. Bacteria were treated with HBc147-183 (1×MBC). The viability of bacteria was measured at indicated time points. Samples were measured in triplicates.

FIGS. 3A-G show localization of FITC-HBc147-183 peptide on bacteria. Approximate $10^7$ CFU of P. aeruginosa ATCC9027, ATCC27853 (3A and 3B), K. pneumoniae ATCC13884 (3C), E. coli ATCC25922 (3D), and S. aureus ATCC19636, ATCC25923 and ATCC 29213 (3E, 3F and 3G) were incubated with HBc147-183 (0.5×MBC) for 1 hour. The bacteria were washed, fixed and stained with DAPI (blue). Images were taken using confocal microscopy.

FIGS. 4A-C show possible bactericidal mechanisms of HBc147-183. (4A) SYTOX Green uptake of P. aeruginosa, K. pneumoniae, E. coli, and S. aureus by HBc147-183. Measurements of the fluorescence were recorded every minute. (4B) Dose-dependent curves of membrane permeabilization of P. aeruginosa by HBc147-183 and HBc153-176 at 0.5, 1 and 2 µM. Two µM melittin was used as a positive control. Samples were measured in triplicates. (4C) DNA-binding activity of HBc147-183. HBc147-183 was mixed with pSUPER plasmid DNA at indicated N/P ratio for 30 minutes. The mobility of DNA was determined by a gel retardation assay.

FIG. 5 shows dose response effects of LPS and LPS antibody on the bactericidal activity of HBc147-183. LPS from *P. aeruginosa* and *E. coli*, and LPS antibody were mixed with *P. aeruginosa* and HBc147-183 (1×MBC) for 3 hours. The bacteria were then plated on MH agar for the measurement of viability. Samples were measured in triplicates.

FIGS. 6A-E show the ARD peptide HBc147-183 being capable of binding to LPS and Lipid A in several different in vitro binding assays. Samples were measured in triplicates in each assay. (6A) The cartoon illustrates the in vitro assays of peptide-LPS and peptide-Lipid A binding as well as LPS/Lipid A competition. (6B) Constant amount of LPS was incubated with increasing concentrations of biotinylated ARD HBc 147-183 peptide on the streptavidine-conjugated beads (0, 0.004, 0.02, 0.1, 0.5 and 2.5 µM). Unbound LPS in the supernatant was measured with the LAL ELISA assay. The EU values were normalized with a control without peptide treatment. HBc147-183 8p (containing 8 phosphorylated amino acids) was also included as a control peptide due to its poor binding with LPS. (6C) Beads-bound LPS was released into the supernatant by overnight digestion with trypsin agarose. Free LPS in the supernatant was analyzed with the LAL ELISA assay. Released LPS in the supernatant appeared to be in proportion to the amount of ARD peptide HBc147-183 on the beads. (6D) Constant amount of Lipid A was incubated with increasing concentrations of HBc147-183 and HBc147-183 8P, respectively. The supernatant was also detected with LAL ELISA reagent. The result here is consistent with the notion that Lipid A can bind to HBc147-183 directly. (6E) LPS/Lipid A competition assay. Constant amount of LPS (1 µg) was coated on each well on the ELISA plate, and then incubated with a reaction mixture containing constant amount of 10 nM HBc147-183 and increasing concentrations of Lipid A. The gradual increase of Lipid A reduced the amount of plate-bound ARD peptide HBc147-183 in a dose dependent manner.

FIGS. 7A-D shows cytotoxicity assays of ARD peptide HBc147-183. (7A) Hemolytic activities of HBc147-183 and melittin were measured with 10% human red blood cells (RBC). Compared to melittin, HBc147-183 showed no hemolytic activity. (7B) Huh7, HepG2, Vero and HEK293 cells were incubated with varying concentrations (0 to 100µM) of HBc147-183 and melittin for 1 hour at 37° C. The effects on cell viability were determined by MTT assay. Melittin was used as a positive control. HBc147-183 showed no detectable effect on cell viability, while melittin exhibited strong toxicity. (7C) Kidney cells, Vero and HEK293 were stained with CFSE and seeded at day 0. At day 1, cells were incubated with varying concentrations (0 to 100 µM) of HBc147-183 for 1 hour. Cell proliferation at day 1 and day 3 were determined by flow cytometry. Similar to the mock control experiment, no significant effect on Vero and HEK293 cells was detected. Samples assayed in FIGS. 7A-C were measured in triplicates. (7D) In vivo toxicity of ARD peptide HBc147-183 was determined using three-week old male ICR mice. The mice were injected intraperitoneally with peptide (10 and 20 mg/kg of body weight). All mice were alive after 7 days.

FIGS. 9A-B shows an IVIS analysis of in vivo antimicrobial activity of ARD peptide against *K. pneumoniae*. (9A) *K. pneumoniae*-infected mice were treated with either PBS (n=5) or 10 mg/kg ARD peptide (n=5) at 1 hour post-inoculation. Four hours post-inoculation, mice were anesthetized and imaged. Bacterial load was displayed in the photographic image with an overlay of bioluminescence. False color imaging represents intense luminescence in red, moderate luminescence in green and low luminescence in blue and purple. (9B) Total flux was quantified by IVIS imaging software. **P,0.01 (Mann-Whitney U test) for PBS and ARD peptide HBc147-183.

FIG. 10 is a table showing antimicrobial activity of HBC ARD peptides.

FIG. 11 is a table showing antimicrobial activity of ARD peptide HBc147-183 against colistin-resistant and sensitive *P. aeruginosa* and *A. baumannii*.

FIG. 12 shows sequence alignments of human hepatitis B virus (HBV) core protein (HBc) arginine rich domain (ARD). HBc ARD domain is highly conserved among different serotypes isolated from patients of different geographic areas.

FIGS. 13A-B show sequence alignments of HBc ARD domains of hepadnaviruses from primate, rodent and avian origins. HBc ARD sequences are highly conserved among human, wooly monkey, ground squirrel, woodchuck, and bat. The arginine (positive charge) clustering subdomains at HBc ARD are designated as ARD-I, ARD-II, ARD-III, and ARD-IV. FIG. 13 B further shows that there are also four clustering positive charge amino acids in the core protein C-terminus of duck, heron, parrot, Ross's goose and snow goose hepatitis B virus. Despite the sequence divergence and evolutionary distance between the primate, rodent, and avian hepadnaviruses, it is contemplated that these positive charge-rich domain at the C-terminus of core protein from rodent (13A) and avian (13B) hepadnaviruses could also contain antimicrobial activities (cf Table 1).

DETAILED DESCRIPTION OF THE INVENTION

Figure 8A:
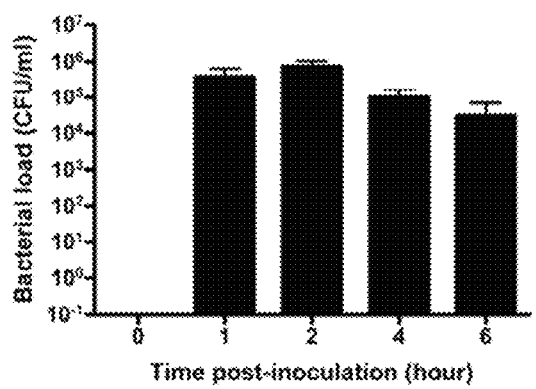
FIGS. 8A-D show in vivo studies of the protection activity of ARD peptide HBc147-183 against *S. aureus*. (8A) Three-week old male ICR mice were challenged with a lethal dose of *S. aureus* ATCC 19636 and then divided into five separate groups for five different time points. At each indicated time point (n=5), blood samples were collected, diluted and plated on BHI agar. The number of bacteria was counted the following day. A maximal bacterial load in the blood was observed at 2 h post-inoculation. The data were shown in mean 6 SD. (8B) ICR mice inoculated with a lethal dose of *S. aureus* as described above were treated by intraperitoneal injection with ARD peptide (10 mg/kg) at 1, 1.5 or 2 h post-inoculation, respectively. Each group contained 10 mice. All mice (100%) treated with the PBS control died at day 1, while treatment of ARD peptide at 1, 1.5 or 2 h post-inoculation protected the mice with survival rates of 100%, 70% and 40% after 7 days, respectively. (8C) As described above, ICR mice were i.p. inoculated with *S. aureus*, followed by i.p. injection with PBS (n=5) or 10 mg/kg ARD peptide (n=5) at 1 h post-inoculation. At 4 h post-inoculation, blood, liver and spleen were collected. Liver and spleen samples were homogenized, diluted and, together with blood samples, plated on BHI agar. The number of bacteria was counted the following day. In comparison to mice treated with PBS, treatment of ARD peptide effectively reduced the bacterial load in blood, liver and spleen. (8D) Quantitative comparison of bacterial loads in blood, liver and spleen samples of mice treated with PBS (open circle, diamond and square) versus ARD peptide HBc147-183 (solid circle, diamond and square). The line indicated the mean of bacterial load. **P,0.01 (Mann-Whitney U test) for PBS and ARD peptide HBc147-183.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Antimicrobial activity refers to the activity to kill or inhibit the growth of microorganisms such as bacteria, fungi and/or protozoans.

As used herein, the term "the arginine-rich carboxy-terminal region of hepatitis B virus core protein (HBc)" refers to a highly conserved arginine-rich C-terminal region of HBc (FIGS. 12 and 13A-B) and is characterized by having an antimicrobial activity. It is contemplated that the arginine-rich carboxy-terminal regions from avian and/or rodent hepadnaviruses share the same antimicrobial activities. The C-terminal end of HBc contains four arginine-rich clusters designated as ARD I-IV. Each arginine-rich cluster or domain (ARD) contains 2 or more arginine residues in continuity or in close proximity (e.g., being separated by one or two different amino acid residues). In one embodiment, each ARD may contain 2,3 or 4 continuous arginine residues.

As used herein, "an amino acid sequence derived from HBc" refers to "an amino acid sequence originates from hepatitis B virus core protein and possess an antimicrobial activity". It may be a fragment of HBc, with or without a modification, which contains ARD and possess an antimicrobial activity. A fragment of HBc with a modification includes, but not limited to PEGylation at either N- or C-terminus.

The term "two clusters" and "two repeats" are interchangeable. The term "two clusters of SPRRRR" means "2 repeats of SPRRRR", or "2 SPRRRR".

The term "amphipathic structure" refers to a molecule having hydrophobic and hydrophilic regions.

The HBV is divided into four major serotypes (adr, adw, ayr, ayw) based on antigenic epitopes present on its envelope proteins. The term "serotype" or "serovar" refers to distinct variations within a species of bacteria or viruses or among immune cells of different individuals.

The term "protecting group" refers to a functional group that is attached to a therapeutic protein or peptide to prolong its circulatory time. A protecting group includes, but not limited to, a polyethylene glycol (PEG). PEGylation can also provide water solubility to hydrophobic proteins or peptides.

The term "treating" or "treatment" refers to administration of an effective amount of a therapeutic agent to a subject in need thereof with the purpose of cure, alleviate, relieve, remedy, ameliorate, or prevent the disease, the symptoms of it, or the predisposition towards it. Such a subject can be identified by a health care professional based on results from any suitable diagnostic method.

"An effective amount" refers to the amount of an active agent that is required to confer a therapeutic effect on the treated subject. Effective doses will vary, as recognized by those skilled in the art, depending on routes of administration, excipient usage, and the possibility of co-usage with other therapeutic treatment.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

$$HED = \text{animal dose in mg/kg} \times (\text{animal weight in kg/human weight in kg})^{0.33}.$$

For example for i.p. administration, if a mouse (20 gram BW) dose is 10 mg/kg, then an human dose may be calculated as $10 \text{ mg/kg} \times (0.02/\text{patient's body weight})^{0.33}$. A human equivalent effective dose, however, may vary, depending on other factors such as the route of administration.

It was an unexpected discovery and unsolved mystery that the growth of *E. coli* expressing HBc1-183 was very poor and much slower than that of *E. coli* expressing HBc1-149. It appeared that it was HBc 150-183 that somehow retarded the growth of *E. coli*, and reduced HBc 1-183 protein yield dramatically. Here, we disclose the in vitro antimicrobial activities of HBc147-183 against a wide variety of bacteria, including multidrug resistant (MDR) and colistin (polymyxin E)-resistant *A baumannii*. The antimicrobial peptides from HBV core protein (HBc) arginine-rich domain (ARD) are mainly composed of SPRRR repeats and are effective against both Gram-positive and Gram-negative bacteria, as well as fungi. Using a peritoneal sepsis mouse model, it was demonstrated further that ARD peptides can effectively protect all the mice challenged with a lethal dose of *Staphylococcus aureus*. Treatment of ARD peptides also caused significant reduction of bacterial load of *S. aureus* and *K. pneumoniae* in infected mice. Potential mechanisms for the bactericidal activity were investigated. The ARD peptides appeared to be capable of direct binding to the Lipid A moiety of lipopolysaccharide (LPS) in several different binding assays. In summary, with high antimicrobial activity and very low toxicity against human cells and animal models, these HBc ARD peptides may have a therapeutic potential in the future (Chen et al. "Identification of a Novel Antimicrobial Peptides from Human Hepatitis B Virus Core Protein Arginine-Rich Domain (ARD)" PLoS Pathog 9(6): e1003425, which is incorporated herein by reference in its entirety).

In one aspect, the invention relates to a pharmaceutical composition comprising:
(a) an effective amount of an isolated peptide, wherein the peptide comprises the arginine-rich carboxy-terminal region of hepatitis B virus core protein (HBc) and exhibits an antimicrobial activity; and
(b) a pharmaceutically acceptable carrier.

In another aspect, the invention relates to a pharmaceutical composition comprising:
(a) an effective amount of an isolated peptide comprising a fragment of HBc, the fragment comprising more than one arginine-rich domain (ARD) selected from the group consisting of (i), (ii) and (iii) as follows:
(i) HBc ARD I-IV;
(ii) HBc ARD I-III; or
(iii) HBc ARD II-IV;
wherein the peptide exhibits an antimicrobial activity; and
(b) a pharmaceutically acceptable carrier.

The HBc may be selected from the group consisting of a mammalian HBc and an avian HBc. A mammalian HBc includes, but not limited to, human hepatitis B core protein (HBc), woolly monkey HBc, ground squirrel HBc, woodchuck HBc, and bat HBc. An avian HBc includes, but not limited to, duck, heron, parrot, Ross's goose, and snow goose.

In another aspect, the invention relates to a pharmaceutical composition comprising an effective amount of an isolated peptide, the peptide comprising an arginine-rich sequence derived from the C-terminal region of hepatitis B virus core protein (HBc), wherein the peptide is characterized by having an antimicrobial activity.

Further in another aspect, the invention relates to a pharmaceutical composition as aforementioned for use in killing and/or inhibiting the growth and/or proliferation of a microorganism by causing the composition to be in contact with the microorganism. The microorganism may be present in a subject.

Yet in another aspect, the invention relates to a pharmaceutical composition as aforementioned for use in killing and/or inhibiting the growth and/or proliferation of a microorganism in a subject in need thereof, or for treating a subject afflicted with a microbial infection. The subject may be afflicted with *Staphylococcus aureus* or *K. pneumoniae* infection.

The antimicrobial peptide according to the invention contains few or no hydrophobic amino acids, and thus has no amphipathic structure.

In one embodiment of the invention, the peptide comprises the amino acid sequence of Ser Pro Arg Arg Arg Arg (SPRRRR; SEQ ID NO: 13) or Arg Arg Arg Ser (RRRS; SEQ ID NO: 14).

Alternatively, the peptide may comprise two clusters of SPRRRR (SEQ ID NO: 13), or three clusters of SPRRR (SEQ ID NO: 15). The peptide may comprise RRRS (SEQ ID NO: 14).

In another embodiment of the invention, the peptide comprises at least 2 clusters of Pro Arg (PR) located upstream to the sequence RRRS (SEQ ID NO: 14). The at least 2 clusters of PR may be immediately adjacent to, or nearby the RRRS sequence with a few residues apart, such as 7, 8, 9, 10, 11, 12, 13, 14, 15, 16, 17 or 18 amino acid residues apart.

The peptide has no RRGGRRRR sequence (SEQ ID NO: 17) at the C-terminus thereof. The peptide may comprise a protecting group.

In another embodiment of the invention, the peptide has a cysteine (C) at the C-terminus thereof.

In another embodiment of the invention, the peptide has at least 19 amino acids but no more than 37 amino acids in length.

In another embodiment of the invention, the peptide is characterized by having an activity against Gram-negative bacteria, Gram-positive bacteria, and/or fungi.

In another embodiment of the invention, the peptide comprises more than one HBc arginine-rich domain selected from the group consisting of (i), (ii) and (iii) as follows:
(i) HBc ARD I, II, III, and IV;
(ii) HBc ARD I, II and III; or
(iii) HBc ARD II, III, and IV.

The peptide comprises 3 or 4 ARD. In another embodiment of the invention, the peptide exhibits an activity against colistin-resistant *A. baumannii*.

In another embodiment of the invention, the peptide is free of the sequence of SQSRESQC (SEQ ID NO: 16) at the C-terminus thereof and is characterized by having an activity against Gram-negative bacteria.

Alternatively, the peptide may comprise HBc ARD II-IV but without HBc ARD I and exhibits an activity against *P. aeruginosa*, or the peptide may comprise HBc ARD I-III but without HBc ARD IV and exhibits an activity against *K. pneumonia*.

In another embodiment of the invention, the peptide exhibits the following characteristics:
i) a reduced antimicrobial activity provided that the Ser in one of the two SPRRRR (SEQ ID NO: 13) clusters is phosphorylated; and/or
ii) a loss of antimicrobial activity provided that the Ser in each SPRRR (SEQ ID NO: 15) cluster is phosphorylated.

The peptide exhibits bactericidal activity and has no cytotoxicity to red blood cells, kidney cells, and/or liver cells.

In another embodiment of the invention, the aforementioned peptide comprises: i) Ser or Pro amino acid residues downstream to the ARD IV at the C-terminal portion of the peptide. The peptide may further comprise: ii) Ser and/or Pro amino acid residues between each ARD (i.e., between ARD I and II, between ARD II and III, and between ARD III and IV.

In another embodiment of the invention, the Ser residue in the amino acid sequence of the peptide is not phosphorylated.

The composition may be formulated for topical, aerosol, oral, systemic intravenous, ocular, or rectal administration, or for inhalation administration.

In another embodiment of the invention, the peptide comprises the amino acid sequence selected from the group consisting of SEQ ID NOs: 1-10, and any serotype thereof.

The amount of the peptide in the composition is effective in killing and/or inhibiting the growth and/or proliferation of Gram-negative bacteria, Gram-positive bacteria, and/or fungi.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

MATERIALS AND METHODS

All animal experiments were conducted under protocols approved by Academia Sinica Institutional Animal Care & Utilization Committee (ASIACUC permit number 12-02-322). Research was conducted in compliance with the principles stated in the Guide for the Care and Use of Laboratory Animals, National Research Council, 1996.

Bacterial Isolates

The antimicrobial activities of HBc ARD peptides were tested on numerous bacterial strains from ATCC, including *Pseudomonas aeruginosa* Migula strain (ATCC 27853, ampicillin-resistant), *Pseudomonas aeruginosa* Migula strain (ATCC 9027, ampicillin-resistant), *Klebsiella pneumoniae* strain (ATCC 17593), *Escherichia coli* strain (ATCC 25922), *Staphylococcus aureus* subsp. strain (ATCC 25923, methicillin-resistant), *Staphylococcus aureus* subsp. strain (ATCC 29213, methicillin-resistant), *Staphylococcus aureus* subsp. strain (ATCC 19636, methicillinresistant), and *Candida albicans* strain (ATCC 10231).

Clinical isolates of *Pseudomonas aeruginosa* (NHRI-01, NHRI-02 AND NHRI-04) were obtained through the program of Taiwan Surveillance of Antimicrobial Resistance, National Health Research Institutes, Taiwan. *Acinetobacter baumannii* (ATCC 17989, ATCC 17978 CR, ATCC19606, ATCC 19606 CR, TCGH 45530 AND TCGH 46709) were obtained from Tzu-Chi Buddhist General Hospital in Taiwan, and clinical isolates (TCGH 45530 AND TCGH 46709) were identified using the Vitek system (Biomerieux Vitek, Inc., MO, USA). *A. baumannii* is defined as multi-drug-resistant when the organism is resistant to piperacillin, piperacillin-tazobactam, ampicillin/sulbactam, imipenem, ceftazidime, gentamicin, amikacin, tetracycline, chloramphenicol, ciprofloxacin, and cotrimoxazole. Susceptibility to colistin was determined using the broth-dilution method, in accordance with the guidelines of the Clinical and Laboratory Standards Institute.

Antimicrobial Activity

All peptides were purchased from Yao-Hong Biotechnology Inc. (Taipei, Taiwan). Vendors provided data of peptide characterizations, including HPLC and Mass. Antimicrobial activity was determined as described with some modifications as detailed below. Bacteria were grown overnight in Mueller-Hinton broth (Difco) at 37° C., and during the mid-logarithmic phase, bacteria were diluted to $10^6$ CFU (colony formation unit)/ml in phosphate buffer (10 mM sodium phosphate and 50 mM sodium chloride, pH 7.2). Peptides were serially diluted in the same buffer. Fifty microliter (µl) of bacteria was mixed with fifty µl of peptides at varying concentrations followed by incubation at 37° C. for 3 hours without shaking. At the end of incubation, bacteria were placed on Mueller-Hinton broth agar plates, and allowed growth at 37° C. overnight for measurement of minimal bactericidal concentration (MBC). The lowest peptide concentration on the agar plate, which displayed no bacterial growth (zero colony), was defined as MBC. All peptides were tested in triplicate.

For measurement of killing kinetics, bacteria and peptides were prepared as described above. Fifty µl of bacteria were mixed with fifty pl of peptides at the concentrations corresponding to MBC and were incubated at 37° C. At the indicated time, bacteria were serially diluted and placed on Mueller-Hinton broth agar plates for viability measurement.

Confocal Fluorescence Microscopy

The localization of peptide was monitored by confocal fluorescence microscopy. Bacteria were grown to mid-logarithmic phase and collected by centrifugation. Approximate $10^7$ CFU were resuspended in a phosphate buffer containing FITC-labeled HBc147-183 at a concentration corresponding to 0.5×MBC. Following incubation for 1 hour at 37° C., cells were washed, fixed, and immobilized on poly-L-lysine coated glass slides. ProLong Gold antifade reagent with DAPI (Invitrogen) was added to the slides prior to mounting. Localization of labeled-peptide was observed using an Olympus Ultraview confocal microscopy equipped with a 100× oil immersion lens.

SYTOX Green Uptake

Briefly, bacteria ($10^7$ CFU) were prepared and mixed with 1 µM SYTOX Green (Invitrogen) for 15 minutes in the dark. After the addition of peptides to the final concentrations corresponding to their respective MBC, fluorescence intensity was measured at 37° C. using wavelengths 485 nm and 520 nm filters for excitation and emission. Melittin (Sigma), a major toxin of bee venom, was used as a positive control to provide maximal permeabilization.

Gel Retardation Assay

The proportion between amino nitrogen ($NH_3^+$) of HBc147-183 and phosphate ($PO_4^-$) of DNA was defined as N/P ratio. Briefly, HBc147-183 was incubated with pSUPER plasmid DNA at different N/P ratio (0, 0.2, 0.4, 0.6, 0.8, 1, 2, 3 and 4) for 30 minutes at 37° C. The mobility of pSUPER plasmid DNA was analyzed by electrophoresis on 1% agarose gel.

In Vitro Binding Assay Between ARD Peptides and LPS/Lipida

Several kinds of peptide-LPS or peptide-Lipid A binding assays were performed as follows:
1) Streptavidine-conjugated beads (Dynabeads MyOne Streptavidin T1, Invitrogen) were blocked by *P. aeruginosa* LPS (Sigma) at 37° C. for 1.5 hour. After washing with PBST (PBS, pH 7.4 containing 0.1% (w/v) Tween-20), aliquots containing 250 pmol streptavidine-conjugated beads were incubated with a reaction mixture overnight at 4° C. The reaction mixture was prepared by mixing increasing amounts of biotinylated peptide HBc147-183 (0, 0.004, 0.02, 0.1, 0.5 and 2.5 µM) and 5 µg/ml *P. aeruginosa* LPS (Sigma) or 200

µg/ml *E. coli* lipid A (Sigma), at 37° C. for 3 hour. After incubation overnight at 4° C., the reduction of LPS (or Lipid A) in the supernatants were measured by the Limulus Amebocyte Lysate (LAL) test (Charles River Endosafe) with an ELISA reader (Molecular Devices). The amount (EU/ml) of LPS was calculated according to the standard curve prepared with Endosafe Control Srandard Endotoxin.

2) To directly measure the increasing amounts of LPS bound to the increasing amounts of peptide HBc147-183 on the peptide-coated beads, the beads were then washed with PBST three times and incubated with 100 µl of PBS containing 0.15 units of trypsin agarose (Sigma) for overnight digestion at 37° C. After trypsinization, the trypsin-released LPS in the supernatants were collected and measured by the Limulus Amebocyte Lysate (LAL) test. Similar results were obtained by another LPS testing method: Endosafe-PST Cartridges (Charles River Laboratories).

3) To perform the LPS/Lipid A competition assay, one µg of LPS was coated on High Binding ELISA plates (Corning) overnight at 4° C. The LPS-coated plates were washed by PBST and then blocked with PBST containing 5% BSA for 1 hour at 37° C. After washing, HBc147-183 (10 nM), mixed with varying concentrations of *E. coli* Lipid A (0 to 10 µg/ml), were added into each well and incubated for 1 hour at 37° C. Plate-bound HBc147-183 was measured by streptavidin conjugated with HRP (1:10000 dilution) for 1 hour at 37° C. TMB substrates were added into each well for color development. The absorption was measured at 450 nm with a reference wavelength at 655 nm.

Hemolytic Activity

The hemolytic activities of peptides were determined by hemolysis against human red blood cells (hRBCs). Human blood was obtained in EDTA-containing tube and was centrifuged at 450 g for 10 min. The pellet was washed three times with PBS buffer, and a solution of 10% hRBCs was prepared. hRBCs solution was mixed with serial dilutions of peptides in PBS buffer, and the reaction mixtures were incubated for 1 h at 37° C. After centrifugation at 450 g for 10 min, the percentage of hemolysis was determined by measuring the absorbance at the wavelength of 405 nm of the supernatant. Blank and 100% hemolysis were determined in PBS buffer and in the presence of 1% Triton X-100, respectively.

Cytotoxicity

Cytotoxicity was measured in HepG2, Huh7, HEK293, and Vero cells by MTT assay. Cells were seeded at $10^4$ cells/well in a 96-well plate and serial dilutions of peptides were added into each well. PBS was used as a negative control and melittin was used as a positive control. After 1 hour of incubation, the medium were replaced by a fresh medium containing 10% MTT solution (PROMEGA™), and the plate was incubated for 4 hours in 5% $CO_2$ at 37° C. The absorbance at the wavelength of 595 nm was measured by an ELISA reader (BIO-RAD™ model 680).

CFSE Cell Proliferation Assay

To set up CFSE cell proliferation assay, 293 cells (human kidney origin) and Vero cells (monkey kidney origin) were resuspended in PBS to a final concentration of $10^6$ cells/ml before incubation with 10 µM CFSE dye (CELLTRACE™ CFSE cell proliferation kit, INVITROGEN™) at 37° C. for 10 min. To quench the staining, ice-old culture media were then added and incubated on ice for 5 min. Labeled cells were then pelleted and washed three times with a fresh medium containing 10% FBS before seeding into six well plates at a density of $3.3 \times 10^5$ cells/well. After 20 h, the medium was removed and incubated with a fresh medium containing 5, 25 and 100 µM HBc 147-183 for one hour (FITC-labeled ARD peptide had been largely internalized in 10 minutes after the addition of ARD peptides to the medium of HepG2 cells). Forty-eight hours later, cells were harvested and analyzed by flow cytometry (FACSCanto, BD Bioscience).

In Vivo Animal Studies

Three-week old male ICR mice (19 to 21 g) were purchased from BioLASCO (Taiwan). Overnight culture of bacteria in BHI broth (Difco) was subcultured in fresh BHI broth to log phase. Inoculums were diluted in BHI broth to indicated densities. To test the acute toxicity of ARD peptide in vivo, ICR male mice were inoculated intraperitoneally (i.p.) with 10 and 20 mg/kg HBc147-183 in PBS, respectively. Each group contained 5 mice. After peptide injection, the number of dead mice was recorded daily for 7 days post-injection. To test the antimicrobial activity of the ARD peptide in vivo, all mice were inoculated i.p. with *Staphylococcus aureus* ATCC 19636 ($4 \times 10^6$ CFU/mouse) in BHI broth. Peptide HBc147-183 (10 mg/kg) was administered i.p. at 1, 1.5 and 2 hours post-inoculation. PBS (10 ml/kg) control was administered at 1 hour post-inoculation. Each group contained 10 mice. Mortality was monitored daily for 7 days post-inoculation. In a separate experiment to measure the bacterial load, mice were inoculated i.p. with *Staphylococcus aureus* ATCC 19636 ($10^6$ CFU/mouse) in BHI broth. All mice were administered at 1 hour post-inoculation with peptide HBc147-183 (10 mg/kg) or PBS (10 ml/kg) control, and sacrificed at 4 hours post-inoculation. Blood samples (200 µl) were mixed with 100 mM EDTA (10 µl) and were diluted 20-fold in PBS ($Ca^{2+}$ and $Mg^{2+}$ free). Liver and spleen samples (0.1 g) were homogenized in sterile PBS (500 µl). Samples were diluted approximately 100-fold and plated on BHI agar for scoring the colony numbers.

To test the in vivo antimicrobial activity of the ARD peptide against Gram-negative bacteria, mice were inoculated with *Klebsiella pneumoniae* Xen39 ($10^7$ cfu/mouse) (Caliper LifeSciences), an engineered strain containing a modified *Photorhabdus luminescens* luxABCDE operon. One hour post-inoculation, mice received either 10 ml/kg PBS (n=5) or 10 mg/kg ARD peptide (n=5), respectively. In vivo imaging was carried out at 4 hours post-inoculation. The mice were anesthetized first before transferring to the IVIS imaging system (IVIS spectrum), and luminescence was measured with an exposure time of 1 minutes or less. The image system measured the number of photons and translated the data to false color images that depicted the region of strong luminescence with red, moderate luminescence with yellow and green, and mild luminescence with blue. Decreasing bioluminescence indicated reduction of bacteria. The images were overlay of photographic images and bioluminescence using a computer-generated color scale. Total flux (RLU) of region of interest (ROI) was quantified by the IVIS imaging software.

RESULTS

In Vitro Antimicrobial Activity of HBc Peptides

As shown in FIGS. 1 and 10, HBc147-183 displayed a broad-spectrum activity against Gram-negative bacteria (*P. aeruginosa, K. pneumoniae* and *E. coli*), Gram-positive bacteria (*S. aureus*), and fungi (*C. albicans*). Among these tested strains, *P. aeruginosa* and *K. pneumonia* were the most sensitive to this peptide. The MBCs of HBc147-183 were lower than 4 µM for *P. aeruginosa* and *K. pneumonia*, and around 4 µM for *E. coli*, and *S. aureus*. *C. albicans* was the least sensitive to this peptide (MBC ~8 µM).

To further map the active sequences of the antimicrobial activity, various peptides (FIG. 1) in different length were synthesized and tested as before. Peptide HBc147-175, with the deletion of the last eight amino acids at the C-terminus, maintained strong activity against Gram-negative bacteria, albeit it lost the activity against *S. aureus* and *C. albicans*. We detected no activity against all of the tested bacteria and fungi from peptides ARD I-II (HBc147-159) or ARD III-IV (HBc164-176 and HBc162-175). In contrast, all peptides containing ARD II-IV (HBc153-176, HBc157-176, HBc153-175, HBc155-175, and HBc157-175) and ARD I-III (HBc147-167) exhibited strong activity against *P. aeruginosa* and *K. pneumonia*, respectively, albeit they were weak against *E. coli* (FIG. 10). Therefore, peptide ARD II-IV and ARD I-III appeared to be necessary and sufficient for the bactericidal activity against *P. aeruginosa* and *K. pneumonia*.

Positive Charge of ARD Peptides is Critical to the Bactericidal Activity

Phophorylation studies on serine residues S155, S162, S170, S176 and S181 revealed that serine phosphorylation in general weakened the potency of antimicrobial activity. It was found that all HBc peptides, once phosphorylated, lost their activities against *C. albicans* (FIG. 11). For bacteria, the phosphorylation on S181 showed no effects, whereas phosphorylations on S155, S162, S170, and S176 reduced the antimicrobial activity. The MBCs dropped to 8 µM for HBc155p and HBc176p, and 32 µM for HBc162p and HBc170p, respectively. When S155, S162 and S170 were simultaneously phosphorylated (HBc155p162p170p), the antimicrobial activity was completely lost (>32 µM). The results suggested that, except for S181, serine phosphorylation is generally detrimental to the antimicrobial activity of HBc ARD peptide. To confirm the importance of arginine residues for bactericidal activity, we synthesized and tested peptide HBc147-183-III-IV AA, which has two R-to-A substitution mutations in each of ARD III and ARD IV. Similar to phosphorylated HBc ARD peptides, the MBC of HBc147-183-III-IV AA was significantly increased compared to HBc147-183. The result indicated that arginine residues are required for the antimicrobial activity.

Drug Resistance

The antimicrobial activity of HBc147-183 against colistin-resistant *P. aeruginosa* and *A. baumannii* was tested. As shown in FIG. 11, while HBc147-183 killed colistin-sensitive *P. aeruginosa* at 4 µM, colistin-resistant *P. aeruginosa* were cross-resistant to HBc147-183 (MBC>16 µM). In contrast to *P. aeruginosa*, the MBCs of HBc147-183 against colistin-sensitive and colistin-resistant *A. baumannii* are in a similar range of 0.5-1 µM. This result indicates that, for colistin-resistant *A. baumannii*, there is no cross-resistance to our ARD peptide HBc147-183.

Killing Kinetics

Time course of bacterial viability was determined after the tested bacteria (*P. aeruginosa, K. pneumonia, E. coli* and *S. aureus*) were treated with HBc147-183 at the concentrations corresponding to the MBC (FIG. 2). The results showed that *P. aeruginosa* was immediately killed within 20 minutes upon the addition of HBc147-183 (2 µM). Although *K. pneumonia* and *E. coli* were members of Gram-negative bacteria, they were killed by 4 µM HBc147-183 in 180 minutes. For *S. aureus*, complete killing by 4 µM HBc147-183 was observed in 120 minutes.

Localization and Mechanism of HBc147-183

*P. aeruginosa*, *E. coli* and *S. aureus* were treated with FITC-labeled HBc147-183 corresponding to 0.5×MBC, and the localization of HBc147-183 was visualized using confocal fluorescence microscopy (FIG. 3). The results showed that, upon peptide treatment, *P. aeruginosa, K. pneumonia* and *E. coli* appeared as hollow rods with fluorescence clearly defined bacteria surface, suggesting that HBc147-183 was accumulated on the membrane (FIGS. 3A-D). To understand better the effect of HBc peptides on the membranes, SYTOX Green uptake assay was performed. A significant degree of membrane permeabilization was induced on *P. aeruginosa* upon the addition of 2 µM HBc147-183 (FIG. 4A). Although it was also accumulated on the membrane of *K. pneumonia* and *E. coli*, 4 µM HBc147-183 was not able to induce membrane permeabilization as observed on *S. aureus*. Consistent with the bactericidal activity of HBc147-183 against *P. aeruginosa*, HBc153-176 caused same membrane permeabilization within 10 minutes in a dose-dependent manner (FIG. 4B). This indicated that the bactericidal effect of HBc peptides on *P. aeruginosa* is directly through the membrane permeabilization with a fast kinetics similar to that of killing kinetics (FIG. 2). On the other hand, HBc147-183 was found to penetrate through the membrane of *S. aureus* and localized in the cytoplasm (FIGS. 3E-G). To investigate the potential interaction between HBc 147-183 and DNA, HBc147-183 was mixed with pSUPER plasmid DNA at different N/P ratio (Materials and Methods) and analyzed by gel electrophoresis (FIG. 4C). The results showed that the mobility of DNA was decreased when the ratio of peptide/DNA increased and the plasmid DNA was completely retarded at the ratio of 1, suggesting that HBc147-183 has a strong binding activity to plasmid DNA. Overall, it suggests that the bactericidal mechanisms of HBc147-183 on Gram-positive and Gram-negative bacteria may be completely different.

Direct Binding of HBc147-183 to LPS

To determine whether LPS of Gram-negative bacteria could serve as a potential target of HBc147-183, LPS (0.05 to 50 µg/ml) from either *P. aeruginosa* or *E. coli* (Sigma) were incubated with both *P. aeruginosa* and 2 µM HBc147-183 for three hours, respectively. The results showed that the bactericidal activity of HBc147-183 was significantly reduced by addition of either LPS at the concentration of 50 µg/ml (FIG. 5). In addition, HBc147-183 preferentially bound to the LPS from *P. aeruginosa*, rather than that from *E. coli*. However, the addition of anti-LPS antibody (Genetex Co.) cannot sufficiently neutralize the bactericidal activity of HBc147-183 (FIG. 5). It suggests that HBc147-183 could bind to not only LPS but also other target molecules on the membrane. Alternatively, HBc147-183 and the anti-LPS polyclonal antibody used here could bind predominantly to two different epitopes on the LPS.

As shown in FIG. 6A, the potential interaction between HBc147-183 and LPS (or Lipid A moiety) in vitro was investigated using several different binding assays. In FIG. 6B, when increasing amount of HBc147-183 was bound to the strepavidine-conjugated Dynabeads and allowed incubation with a constant amount of LPS, gradually increasing amount of LPS appeared to be depleted from the supernatant. HBc147-183 8p, which has eight ser/thr phosphorylations, was used in parallel as a control peptide. Similar results were obtained by another LPS testing method: Endosafe-PTS Cartridges (Charles River Laboratories). In FIG. 6C, the beads-captured LPS were dissociated from the beads by trypsin agarose digestion of the ARD peptide HBc147-183. The amount of released LPS was measured by the LAL test (Materials and Methods). LPS contains mainly the polysaccharide and Lipid A moieties. To determine whether the ARD peptide can bind to Lipid A directly, we tested in FIG. 6D the binding between Lipid A and the ARD peptide in a manner similar to FIG. 6B. As expected, increasing amounts of HBc147-183 on the beads led to decreasing amounts of Lipid A remaining in the supernatant. The inverse correlation between the ARD peptide on the beads and the Lipid A in the supernatant (FIG. 6D) is strikingly similar to what was observed previously between the ARD peptide HBc147-183 on the beads and LPS in the supernatant (FIG. 6B). To directly demonstrate that the ARD peptide can bind to the Lipid A moiety of LPS, we performed a competition experiment between Lipid A and LPS (FIG. 6E). The LPS-coated ELISA plates were incubated with constant amount of HBc147-183 (10 nM), which was pre-mixed with varying concentrations of E. coli Lipid A (0 to 10 µg/ml). After extensive washing, plate-bound (i.e., LPS-bound) biotinylated peptide HBc147-183 was measured by streptavidin conjugated with HRP, followed by adding TMB substrates and color development. The binding of HBc147-183 to LPS was significantly decreased by the increasing concentrations of Lipid A (FIG. 6E). The result here lends support for the notion that Lipid A moiety of LPS can serve as a direct target for ARD peptide HBc147-183.

Cytocoxicity

To determine the cytotoxicity of HBc peptides, we measured the hemolytic activity of HBc147-183. Compared to the melittin control, no detectable hemolysis by HBc147-183 was observed after one hour of incubation (FIG. 7A). In addition, MTT assay was performed to determine the cytotoxicity of HBc147-183 to human hepatoma (Huh 7 and HepG2 cells) and kidney cells (Vero and HEK293 cells). The viability of cells treated with melittin at low dose (3.125 µM) was significantly decreased. In contrast, HBc147-183 caused only a low level of cytotoxicity at the concentration of 100 µM (FIG. 7B). The CFSE cell proliferation assay was also performed to determine the effect of HBc147-183 on the proliferation of Vero and HEK293 kidney cells. In comparison to day 1, CFSE intensity of cells treated with HBc147-183 (5, 25 and 100 µM) decreased to the same level as the mock control on day 3 (FIG. 7C), suggesting that ARD peptide HBc147-183 has no significant effect on cell proliferation.

Animal Model

Figure 8B:
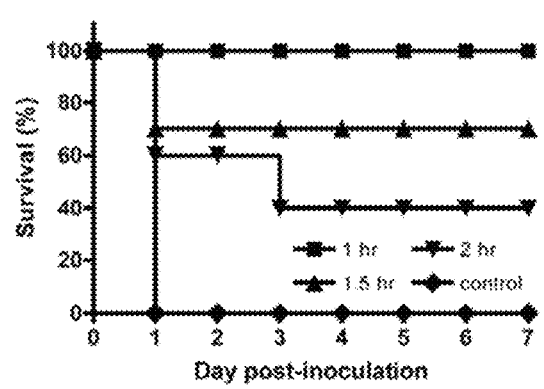
Figure 8C:
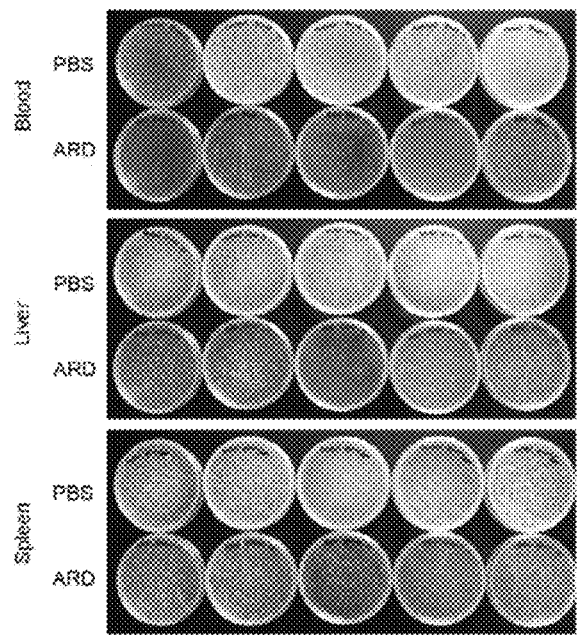
Figure 8D:
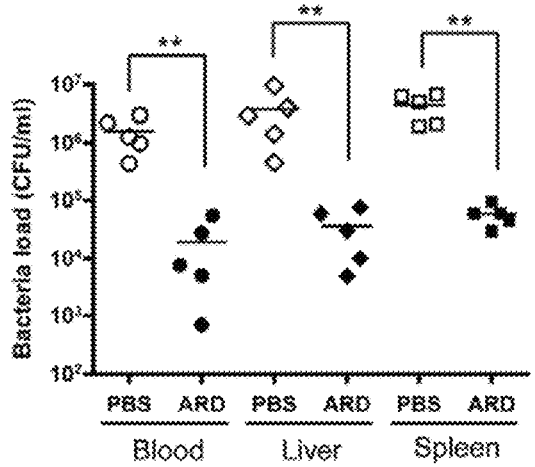

To conduct the experimental infection with bacteria, we i.p. inoculated mice with Staphylococcus aureus ATCC 19636 ($4 \times 10^6$ cfu/mouse). Bacterial load in blood at 1, 2, 4 and 6 hours post-inoculation was determined. As shown in FIG. 8A, bacteria rapidly transferred to the blood compartment from peritoneal cavity. Within 2 hours, the number of bacteria in the blood achieved the maximum ($10^6$ cfu/ml). Thereafter, the number of bacteria in the blood gradually decreased spontaneously. To distinguish the ARD peptide-mediated from the spontaneous clearance, we therefore tested the in vivo protection activity of the ARD peptide within 2 hours post-inoculation. Briefly, mice were i.p. inoculated with Staphylococcus aureus ATCC 19636 and received a single dose of 10 ml/kg PBS or a single dose of 10 mg/kg ARD peptide at 1, 1.5, 2 hours post-inoculation, respectively. Mice (n=10) treated with PBS died within 24 hours post-inoculation (FIG. 8B). In contrast, administration of ARD peptide (10 mg/kg) at 1 hour post-inoculation can effectively protect all mice (n=10) from death at day 7. When we administered ARD peptide at 1.5 (n=10) and 2 (n=10) hours post-inoculation, survival rates were decreased to 70% and 40%, respectively. Instead of using death as a surrogate indicator of the antimicrobial activity of ARD peptide, we also determined directly the in vivo effect of ARD peptide on bacterial load of infected mice (FIG. 8C). Mice were inoculated with Staphylococcus aureus as before and treated with 10 ml/kg PBS (n=5) or 10 mg/kg ARD peptide (n=5) at 1 hour post-inoculation. Four hours post-inoculation, bacterial load in blood, liver and spleen samples of control mice were in the range of $10^6$ cfu/ml (FIGS. 8C and 8D). Administration of ARD peptide significantly reduced the bacterial load (~$10^4$ cfu/ml) by 100-fold in blood, liver and spleen than the PBS control mice (P<0.01). In addition to Staphylococcus aureus, we also examined the in vivo antimicrobial activity of ARD peptide on K. pneumoniae using an IVIS imaging system. Similar to the change in bacterial load of S. aureus, bioluminescence of mice inoculated with K. pneumoniae Xen39 peaked at 2 hour post-inoculation (data not shown). We then treated K. pneumoniae Xen39-infected mice with PBS or ARD peptide at 1 hour post-inoculation, respectively. The results showed that the bioluminescence of ARD peptide-treated mice was very weak, whereas PBS control showed a more extensive bioluminescence (FIG. 9A). There was a significant difference in the overall RLU values of mice treated with PBS versus ARD peptide (P<0.01) (FIG. 9B). Taken together, the results indicated that HBc147-183 exhibited significant antimicrobial activity in vivo. Table 1 shows comparison of minimal bactericidal concentrations of human HBc ARD and woodchuck HBc ARD against Gram-negative and Gram-positive bacteria.

TABLE 1

| Bacteria strain | Minimal bactericidal concentration (µM) | |
| --- | --- | --- |
| | hHBc ARD[1] | wHBc ARD[2] |
| P. aeruginosa ATCC 9027 | 2 | 2 |
| P. aeruginosa ATCC 27853 | 2-4 | 2 |
| K. pneumoniae ATCC 13884 | 2 | 2 |
| E. coli ATCC 25922 | 4 | 4 |
| S. aureus ATCC 19636 | 4 | 8 |

[1]Human hepatitis B virus core protein arginine-rich domain (ARD)
(TVVRRRGRSPRRRTPSPRRRRSQSPRRRRSQSRESQC; SEQ ID NO: 1)
[2]Woodchuck hepatitis B virus core protein ARD
TVIRRRGGARASRSPRRRTPSPRRRRSQSPRRRRSQSPSANC; SEQ ID NO: 4)

The invention relates to a novel antimicrobial peptide (HBc147-183) isolated from the C-terminal domain of HBc. The computer program based on the antimicrobial peptide database (Wang et al. (2004) Nucleic Acids Res 32: D590-592) predicted unfavorably that HBc147-183 could serve as an antibacterial peptide, due to its very low content of hydrophobic amino acids. Contrary to the computer prediction, surprisingly, HBc147-183 exhibited a broad-spectrum antimicrobial activity. While colistin-resistant P. aeruginosa exhibited cross-resistance to ARD peptide HBc147-183, we found a strong activity of hbc147-183 (MBC=0.5-1 µm) against all tested colistin-resistant A. baumannii. Our ARD peptide could bind to Lipid A of E. coli and LPS of P. aeruginosa (FIG. 6). While only the full-length HBc147-183 (ARD I-IV) was effective against the tested gram-positive bacteria, S. aureus, ARD II-IV (HBc153-176) and ARD I-III (HBc147-167), in a less than full-length context, exhibited strong activity against gram-negative P. aeruginosa and K. pneumoniae, respectively (but not E. coli).

Comparisons with Other AMPs

It is surprising that the ARD domain of HBc protein (HBc147-183) exhibits novel and broad spectrum antimicrobial activity. This peptide shares some degree of similarity with several antimicrobial peptides in literature, such as protamine (PRRRRSSSRPVRRRRRPRVSRRRRRRG-GRRRR; SEQ ID NO: 11) and drosocin (GKPRPYSPRPT-SHPRPIRV; SEQ ID NO: 12). A radial diffusion assay showed that a single arginine-rich domain (RRRR) is sufficient for antimicrobial activity, especially against gram-negative bacteria (Lesmes et al. (2009) Peptides 30: 2150-2160). Unlike protamine, the arginine-rich domain of HBc147-183, such as ARD I-II and ARD III-IV, were not sufficient for the antimicrobial activity. In addition, sequence alignment by anitimicrobial peptide database revealed that HBc153-176 shares 44% amino acid sequence homology with Drosocin, which is a proline-rich peptide isolated from Drosophila. However, except for P. aeruginosa, Drosocin is predominately active against most Gram-negative bacteria. Drosocin kills bacteria via an apparently non-membranolytic mechanism. The HBc ARD is a novel peptide with a broad spectrum bactericidal activity quite distinct from other known arginine-rich antimicrobial peptides. Protamine contains RRGGRRRR (SEQ ID NO: 17), while HBc147-183 contains SQSRESQC (SEQ ID NO: 16) at the C-terminus of HBc.

Bactericidal Mechanisms

The results showed the membrane localization of HBc147-183 on Gram-negative bacteria (FIG. 3) and the neutralization activity of LPS from either P. aeruginosa or E. coli (FIG. 5). It suggests that HBc147-183 could have a strong binding activity to LPS. The results revealed a direct binding of HBc147-183 to LPS and Lipid A (FIGS. 6B, 6C and 6D). Furthermore, Lipid A moiety of LPS was shown to be one major direct target of HBc147-183 (FIG. 6E). However, incubation of LPS antibody with P. aeruginosa and HBc147-183 failed to neutralize the bactericidal activity of HBc ARD peptide (FIG. 5). One interpretation for this negative result is that HBc147-183 could bind not only LPS but also some other molecules on the bacterial membrane. We found a better neutralization effect of the LPS from P. aeruginosa than that from E. coli (FIG. 5). The preference of binding by HBc147-183 for the LPS of P. aeruginosa is correlated with its stronger bactericidal activity against P. aeruginosa.

The mode of action of HBc147-183 on P. aeruginosa could be related to membrane permeabilization based on the fast killing kinetics (FIG. 2) and its membrane localization (FIGS. 3A and 3B). This speculation is also supported by the results of SYTOX Green uptake experiment (FIG. 4A). Like P. aeruginosa, HBc147-183 was also accumulated on the membrane of K. pneumonia and E. coli. However, the killing kinetics and SYTOX Green uptake experiments of K. pneumonia and E. coli did not support for a mechanism of membrane permeabilization. It remains to be further investigated how bacteria can be killed by the ARD peptides using a mechanism other than membrane permeabilization.

In the case of Gram-positive bacteria, we found that HBc147-183 was not accumulated on the membrane (FIG. 3). Instead, it can enter the cytoplasm of S. aureus without any apparent development of membrane permeabilization (FIG. 4A). In addition to LPS, HBc147-183 can also bind strongly to plasmid DNA (FIG. 4C). Taken together, the bactericidal mechanism of HBc147-183 against Gram-positive bacteria appeared to be more similar to Buforin II, which was reported to kill bacteria by binding to DNA and RNA after penetrating bacterial membrane.

Although HBc147-183 can penetrate through the cell membrane of Huh 7 and HepG2 cells (data not shown), we observed no significant cytotoxic effect on human hepatoma cells Huh 7 and HepG2, and kidney cells Vero and HEK293, even at a high peptide concentration (100 µM) by MTT assay (FIG. 7B) and proliferation assay (FIG. 7C). Taken together with the results from the hemolytic assay (FIG. 7A), HBc147-183 appears to be much safer relative to melittin in cell culture. The animal model study showed no apparent in vivo toxicity of ARD peptide at 20 mg/kg dose in the ICR mice by i.p. injection (FIG. 7D). At as low as 10 mg/kg level, treatment of ARD peptide can protect mice from death (FIG. 8B). In contrast, all mice receiving the PBS control were dead soon after bacterial inoculation. In addition to the sepsis survival model, treatment of ARD peptide (10 mg/kg) also resulted in a significant reduction of bacterial load of S. aureus and K. pneumoniae, whereas PBS control mice showed high levels of bacterial load (FIGS. 8C-D and FIG. 9). The results demonstrated the in vivo antimicrobial potency of HBc ARD peptide.

What is claimed is:

1. A pharmaceutical composition comprising:
   (a) an isolated peptide consisting of (i) a protecting group and a sequence selected from the group consisting of residues 1-29 of SEQ ID NO: 1, residues 1-21 of SEQ ID NO: 1, residues 7-30 of SEQ ID NO: 1, residues 11-30 of SEQ ID NO: 1, residues 7-29 of SEQ ID NO:1, residues 9-29 of SEQ ID NO: 1, or residues 11-29 of SEQ ID NO: 1, and
   (b) a pharmaceutically acceptable carrier.

2. The composition of claim 1, wherein the peptide contains no amphipathic structure.

3. The composition of claim 1, wherein the peptide exhibits an activity against a gram-negative bacterium.

4. The composition of claim 1, wherein the composition is formulated for topical, aerosol, oral, intravenous, intraperitoneal, ocular, rectal, or inhalation administration.

5. The pharmaceutical composition of claim 1, wherein the peptide consists of a protecting group and residues 1-29 of SEQ ID NO: 1.

6. The pharmaceutical composition of claim 1, wherein the peptide consists of a protecting group and residues 1-21 of SEQ ID NO: 1.

7. The pharmaceutical composition of claim 1, wherein the peptide consists of a protecting group and residues 7-30 of SEQ ID NO: 1.

8. The pharmaceutical composition of claim 1, wherein the peptide consists of a protecting group and residues 11-30 of SEQ ID NO: 1.

9. The pharmaceutical composition of claim 1, wherein the peptide consists of a protecting group and residues 7-29 of SEQ ID NO: 1.

10. The pharmaceutical composition of claim 1, wherein the peptide consists of a protecting group and residues 9-29 of SEQ ID NO: 1.

11. The pharmaceutical composition of claim 1, wherein the peptide consists of a protecting group and residues 11-29 of SEQ ID NO: 1.

12. A method of killing or inhibiting proliferation of a gram-negative bacterium or treating a subject infected with a gram-negative bacterium, comprising administering the pharmaceutical composition of claim 1 to a subject in need thereof.

* * * * *

SEQUENCE LISTING

```
<160> NUMBER OF SEQ ID NOS: 33

<210> SEQ ID NO 1
<211> LENGTH: 37
<212> TYPE: PRT
<213> ORGANISM: Human Hepatitis B virus

<400> SEQUENCE: 1

Thr Val Val Arg Arg Arg Gly Arg Ser Pro Arg Arg Arg Thr Pro Ser
1               5                   10                  15

Pro Arg Arg Arg Arg Ser Gln Ser Pro Arg Arg Arg Arg Ser Gln Ser
            20                  25                  30

Arg Glu Ser Gln Cys
        35

<210> SEQ ID NO 2
<211> LENGTH: 36
<212> TYPE: PRT
<213> ORGANISM: Woolly monkey Hepatitis B virus
```

-continued

```
<400> SEQUENCE: 2

Thr Val Val Arg Arg Arg Pro Ser Gly Arg Arg Thr Pro Ser Pro
1               5                   10                  15

Arg Arg Arg Arg Ser Gln Ser Pro Arg Arg Arg Ser Gln Ser Pro
            20                  25                  30

Ala Ser Ser Cys
            35

<210> SEQ ID NO 3
<211> LENGTH: 41
<212> TYPE: PRT
<213> ORGANISM: Ground squirrel Hepatitis B virus

<400> SEQUENCE: 3

Thr Val Ile Arg Arg Arg Gly Ser Ala Arg Val Val Arg Ser Pro Arg
1               5                   10                  15

Arg Arg Thr Pro Ser Pro Arg Arg Arg Ser Gln Ser Pro Arg Arg
            20                  25                  30

Arg Pro Gln Ser Pro Ala Ser Asn Cys
            35                  40

<210> SEQ ID NO 4
<211> LENGTH: 42
<212> TYPE: PRT
<213> ORGANISM: Woodchuck hepatitis B virus

<400> SEQUENCE: 4

Thr Val Ile Arg Arg Arg Gly Gly Ala Arg Ala Ser Arg Ser Pro Arg
1               5                   10                  15

Arg Arg Thr Pro Ser Pro Arg Arg Arg Ser Gln Ser Pro Arg Arg
            20                  25                  30

Arg Arg Ser Gln Ser Pro Ser Ala Asn Cys
            35                  40

<210> SEQ ID NO 5
<211> LENGTH: 43
<212> TYPE: PRT
<213> ORGANISM: Bat Hepatitis B virus

<400> SEQUENCE: 5

Thr Ile Val Arg Arg Arg Gly Gly Ser Arg Ala Thr Arg Ser Pro Arg
1               5                   10                  15

Arg Arg Thr Pro Ser Pro Arg Arg Arg Ser Gln Ser Pro Arg Arg
            20                  25                  30

Arg Arg Ser Gln Ser Pro Ala Ser Ser Asn Cys
            35                  40

<210> SEQ ID NO 6
<211> LENGTH: 36
<212> TYPE: PRT
<213> ORGANISM: Duck hepatitis B virus

<400> SEQUENCE: 6

Arg Lys Pro Arg Gly Leu Glu Pro Arg Arg Arg Lys Val Lys Thr Thr
1               5                   10                  15

Val Val Tyr Gly Arg Arg Arg Ser Lys Ser Arg Glu Arg Arg Ala Pro
            20                  25                  30

Thr Pro Gln Arg
            35
```

<210> SEQ ID NO 7
<211> LENGTH: 36
<212> TYPE: PRT
<213> ORGANISM: Heron hepatitis B virus

<400> SEQUENCE: 7

Arg Lys Pro Arg Gly Leu Glu Pro Arg Arg Lys Val Lys Thr Thr
1               5                   10                  15

Val Val Tyr Gly Arg Arg Arg Ser Lys Ser Arg Gly Arg Ser Ser
            20                  25                  30

Pro Ser Gln Arg
        35

<210> SEQ ID NO 8
<211> LENGTH: 36
<212> TYPE: PRT
<213> ORGANISM: Parrot Hepatitis B virus

<400> SEQUENCE: 8

Arg Lys Pro Arg Gly Leu Glu Pro Arg Arg Lys Val Lys Thr Thr
1               5                   10                  15

Val Val Tyr Gly Arg Arg Arg Ser Lys Ser Arg Glu Arg Ser Ser
            20                  25                  30

Ser Pro Gln Arg
        35

<210> SEQ ID NO 9
<211> LENGTH: 36
<212> TYPE: PRT
<213> ORGANISM: Ross's goose Hepatitis B virus

<400> SEQUENCE: 9

Arg Lys Pro Arg Gly Leu Glu Pro Arg Arg Lys Val Lys Thr Thr
1               5                   10                  15

Val Val Tyr Gly Arg Arg Arg Ser Lys Ser Arg Glu Arg Ala Pro
            20                  25                  30

Thr Pro Gln Arg
        35

<210> SEQ ID NO 10
<211> LENGTH: 36
<212> TYPE: PRT
<213> ORGANISM: Snow goose Hepatitis B virus

<400> SEQUENCE: 10

Arg Lys Pro Arg Gly Leu Glu Pro Arg Arg Lys Val Lys Thr Thr
1               5                   10                  15

Val Val Tyr Gly Arg Arg Arg Ser Lys Ser Arg Glu Arg Ala Ser
            20                  25                  30

Ser Pro Gln Arg
        35

<210> SEQ ID NO 11
<211> LENGTH: 32
<212> TYPE: PRT
<213> ORGANISM: Oncorhynchus mykiss

<400> SEQUENCE: 11

Pro Arg Arg Arg Arg Ser Ser Ser Arg Pro Val Arg Arg Arg Arg
1               5                   10                  15

Pro Arg Val Ser Arg Arg Arg Arg Arg Gly Gly Arg Arg Arg
            20                  25                  30

<210> SEQ ID NO 12
<211> LENGTH: 19
<212> TYPE: PRT
<213> ORGANISM: Drosophila melanogaster

<400> SEQUENCE: 12

Gly Lys Pro Arg Pro Tyr Ser Pro Arg Pro Thr Ser His Pro Arg Pro
1               5                   10                  15

Ile Arg Val

<210> SEQ ID NO 13
<211> LENGTH: 6
<212> TYPE: PRT
<213> ORGANISM: Hepatitis B virus

<400> SEQUENCE: 13

Ser Pro Arg Arg Arg Arg
1               5

<210> SEQ ID NO 14
<211> LENGTH: 4
<212> TYPE: PRT
<213> ORGANISM: Hepatitis B virus

<400> SEQUENCE: 14

Arg Arg Arg Ser
1

<210> SEQ ID NO 15
<211> LENGTH: 5
<212> TYPE: PRT
<213> ORGANISM: Hepatitis B virus

<400> SEQUENCE: 15

Ser Pro Arg Arg Arg
1               5

<210> SEQ ID NO 16
<211> LENGTH: 8
<212> TYPE: PRT
<213> ORGANISM: Hepatitis B virus

<400> SEQUENCE: 16

Ser Gln Ser Arg Glu Ser Gln Cys
1               5

<210> SEQ ID NO 17
<211> LENGTH: 8
<212> TYPE: PRT
<213> ORGANISM: Oncorhynchus mykiss

<400> SEQUENCE: 17

Arg Arg Gly Gly Arg Arg Arg Arg
1               5

<210> SEQ ID NO 18
<211> LENGTH: 37
<212> TYPE: PRT
<213> ORGANISM: Human Hepatitis B virus

<400> SEQUENCE: 18

```
Thr Val Val Arg Arg Gly Arg Ser Pro Arg Arg Thr Pro Ser
1               5                   10                  15

Pro Arg Arg Arg Arg Ser Lys Ser Pro Arg Arg Arg Ser Gln Ser
                20                  25                  30

Arg Glu Ser Gln Cys
            35

<210> SEQ ID NO 19
<211> LENGTH: 37
<212> TYPE: PRT
<213> ORGANISM: Human Hepatitis B virus

<400> SEQUENCE: 19

Thr Val Val Arg Arg Gly Arg Ser Pro Arg Arg Thr Pro Ser
1               5                   10                  15

Pro Arg Arg Arg Arg Ser Gln Ser Pro Arg Arg Arg Ser Gln Ser
                20                  25                  30

Arg Glu Ser Gln Cys
            35

<210> SEQ ID NO 20
<211> LENGTH: 39
<212> TYPE: PRT
<213> ORGANISM: Human Hepatitis B virus

<400> SEQUENCE: 20

Thr Val Val Arg Arg Arg Asp Arg Gly Arg Ser Pro Arg Arg Arg Thr
1               5                   10                  15

Pro Ser Pro Arg Arg Arg Arg Ser Gln Ser Pro Arg Arg Arg Ser
                20                  25                  30

Gln Ser Arg Glu Ser Gln Cys
                35

<210> SEQ ID NO 21
<211> LENGTH: 37
<212> TYPE: PRT
<213> ORGANISM: Human Hepatitis B virus

<400> SEQUENCE: 21

Thr Val Val Arg Arg Gly Arg Ser Pro Arg Arg Thr Pro Ser
1               5                   10                  15

Pro Arg Arg Arg Arg Ser Gln Ser Pro Arg Arg Arg Ser Gln Ser
                20                  25                  30

Arg Glu Ser Gln Cys
            35

<210> SEQ ID NO 22
<211> LENGTH: 37
<212> TYPE: PRT
<213> ORGANISM: Human Hepatitis B virus

<400> SEQUENCE: 22

Thr Val Val Arg Arg Gly Arg Ser Pro Arg Arg Thr Pro Ser
1               5                   10                  15

Pro Arg Arg Arg Arg Ser Gln Ser Pro Arg Arg Arg Ser Gln Ser
                20                  25                  30

Arg Glu Ser Gln Cys
            35
```

-continued

```
<210> SEQ ID NO 23
<211> LENGTH: 39
<212> TYPE: PRT
<213> ORGANISM: Human Hepatitis B virus

<400> SEQUENCE: 23

Thr Val Val Arg Arg Arg Asp Arg Gly Arg Ser Pro Arg Arg Arg Thr
1               5                   10                  15

Pro Ser Pro Arg Arg Arg Arg Ser Gln Ser Pro Arg Arg Arg Arg Ser
            20                  25                  30

Gln Ser Arg Glu Ser Gln Cys
        35

<210> SEQ ID NO 24
<211> LENGTH: 37
<212> TYPE: PRT
<213> ORGANISM: Human Hepatitis B virus

<400> SEQUENCE: 24

Thr Val Val Arg Arg Arg Gly Arg Ser Pro Arg Arg Thr Pro Ser
1               5                   10                  15

Pro Arg Arg Arg Arg Ser Gln Ser Pro Arg Arg Arg Arg Ser Gln Ser
            20                  25                  30

Arg Glu Ser Gln Cys
        35

<210> SEQ ID NO 25
<211> LENGTH: 37
<212> TYPE: PRT
<213> ORGANISM: Human Hepatitis B virus

<400> SEQUENCE: 25

Ala Val Val Arg Arg Arg Gly Arg Ser Pro Arg Arg Arg Thr Pro Ser
1               5                   10                  15

Pro Arg Arg Arg Arg Ser Gln Ser Pro Arg Arg Arg Arg Ser Gln Ser
            20                  25                  30

Arg Gly Ser Gln Cys
        35

<210> SEQ ID NO 26
<211> LENGTH: 39
<212> TYPE: PRT
<213> ORGANISM: Human Hepatitis B virus

<400> SEQUENCE: 26

Thr Val Val Arg Arg Arg Asp Arg Gly Arg Ser Pro Arg Arg Arg Thr
1               5                   10                  15

Pro Ser Pro Arg Arg Arg Arg Ser Gln Ser Pro Arg Arg Arg Arg Ser
            20                  25                  30

Gln Ser Arg Glu Ser Gln Cys
        35

<210> SEQ ID NO 27
<211> LENGTH: 37
<212> TYPE: PRT
<213> ORGANISM: Human Hepatitis B virus

<400> SEQUENCE: 27

Thr Val Val Arg Arg Arg Gly Arg Ser Pro Arg Arg Arg Thr Pro Ser
1               5                   10                  15

Pro Arg Arg Arg Arg Ser Gln Ser Pro Arg Arg Arg Arg Ser Gln Ser
```

Arg Glu Ser Gln Cys
        35

<210> SEQ ID NO 28
<211> LENGTH: 37
<212> TYPE: PRT
<213> ORGANISM: Human Hepatitis B virus

<400> SEQUENCE: 28

Thr Val Val Arg Gln Arg Gly Arg Thr Ile Arg Arg Thr Pro Ser
1               5                   10                  15

Pro Arg Arg Arg Arg Ser Gln Ser Pro Arg Arg Arg Ser Gln Ser
            20                  25                  30

Arg Glu Ser Gln Cys
        35

<210> SEQ ID NO 29
<211> LENGTH: 37
<212> TYPE: PRT
<213> ORGANISM: Human Hepatitis B virus

<400> SEQUENCE: 29

Thr Val Val Arg Arg Arg Gly Arg Ser Pro Arg Arg Arg Thr Pro Ser
1               5                   10                  15

Pro Arg Arg Arg Arg Ser Gln Ser Pro Arg Arg Arg Ser Gln Ser
            20                  25                  30

Arg Glu Ser Gln Cys
        35

<210> SEQ ID NO 30
<211> LENGTH: 37
<212> TYPE: PRT
<213> ORGANISM: Human Hepatitis B virus

<400> SEQUENCE: 30

Thr Val Val Arg Arg Arg Gly Arg Ser Pro Arg Arg Arg Thr Pro Ser
1               5                   10                  15

Pro Arg Arg Arg Arg Ser Gln Ser Pro Arg Arg Arg Ser Gln Ser
            20                  25                  30

Arg Glu Ser Gln Cys
        35

<210> SEQ ID NO 31
<211> LENGTH: 37
<212> TYPE: PRT
<213> ORGANISM: Human Hepatitis B virus

<400> SEQUENCE: 31

Thr Val Val Arg Arg Arg Gly Arg Ser Pro Arg Arg Arg Thr Pro Ser
1               5                   10                  15

Pro Arg Arg Arg Arg Ser Gln Ser Pro Arg Arg Arg Ser Gln Ser
            20                  25                  30

Arg Glu Ser Gln Cys
        35

<210> SEQ ID NO 32
<211> LENGTH: 37
<212> TYPE: PRT
<213> ORGANISM: Human Hepatitis B virus

```
<400> SEQUENCE: 32

Thr Val Val Arg Arg Arg Gly Arg Ser Pro Arg Arg Arg Thr Pro Ser
1               5                   10                  15

Pro Arg Arg Arg Arg Ser Gln Ser Pro Arg Arg Arg Arg Ser Gln Ser
                20                  25                  30

Arg Glu Ser Gln Cys
            35

<210> SEQ ID NO 33
<211> LENGTH: 37
<212> TYPE: PRT
<213> ORGANISM: Human Hepatitis B virus

<400> SEQUENCE: 33

Thr Val Val Arg Gly Arg Gly Arg Ser Ser Arg Arg Arg Thr Pro Ser
1               5                   10                  15

Pro Arg Arg Arg Arg Ser Gln Ser Pro Arg Arg Arg Arg Ser Gln Ser
                20                  25                  30

Arg Glu Ser Gln Cys
            35
```